(12) United States Patent
Cage et al.

(10) Patent No.: US 10,126,266 B2
(45) Date of Patent: *Nov. 13, 2018

(54) FLUID PARAMETER SENSOR AND METER

(71) Applicant: CONCENTRIC METER CORPORATION, Longmont, CO (US)

(72) Inventors: Donald R. Cage, Longmont, CO (US); Michael N. Schott, Loveland, CO (US); Kristian S. Schartau, Erie, CO (US)

(73) Assignee: Concentric Meter Corporation, Longmont, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/476,238

(22) Filed: Mar. 31, 2017

(65) Prior Publication Data

US 2017/0205373 A1    Jul. 20, 2017

Related U.S. Application Data

(63) Continuation-in-part of application No. 14/981,272, filed on Dec. 28, 2015, now Pat. No. 9,752,911.
(Continued)

(51) Int. Cl.
*G01N 22/02* (2006.01)
*G01N 29/02* (2006.01)
(Continued)

(52) U.S. Cl.
CPC ........... *G01N 29/02* (2013.01); *G01F 1/8422* (2013.01); *G01F 1/8459* (2013.01);
(Continued)

(58) Field of Classification Search
CPC .................................................... G01F 1/849
See application file for complete search history.

(56) References Cited

U.S. PATENT DOCUMENTS

| 1,175,586 A | 3/1916 | Beyler |
| 2,215,566 A | 9/1940 | Schaaf, Jr. |

(Continued)

FOREIGN PATENT DOCUMENTS

| EP | 0222503 | 5/1987 |
| EP | 2612130 | 9/2014 |

(Continued)

OTHER PUBLICATIONS

Written Opinion of the International Searching Authority for co-owned PCT patent application No. PCT/US2015/067710 dated Apr. 29, 2016, 10 pages.
(Continued)

*Primary Examiner* — Jewel V Dowtin
(74) *Attorney, Agent, or Firm* — Trenner Law Firm, LLC; Mark D. Trenner

(57) ABSTRACT

An example fluid parameter sensor and meter is disclosed to measure at least one parameter of a fluid. In an example, the fluid parameter meter includes an outer conduit. A sensor element assembly is disposed in the outer conduit and having a plurality of sensor elements to convey the fluid inside of the sensor element assembly. At least one mounting flexure is fixedly attached to the sensor element assembly and to the outer conduit. The at least one mounting flexure is configured to enable the sensor element assembly to vibrate in a radial motion. At least one vibration driver causes the sensor element assembly to vibrate in the radial motion. At least one vibration sensor senses the radial motion of the sensor element assembly. Controlling electronics measure at least one parameter of a fluid based on said radial motion.

18 Claims, 28 Drawing Sheets

Related U.S. Application Data

(60) Provisional application No. 62/097,209, filed on Dec. 29, 2014.

(51) Int. Cl.
*G01F 1/84* (2006.01)
*G01F 15/02* (2006.01)
*G01N 9/00* (2006.01)

(52) U.S. Cl.
CPC .......... *G01F 1/8463* (2013.01); *G01F 15/022* (2013.01); *G01N 9/002* (2013.01); *G01N 2291/024* (2013.01); *G01N 2291/02818* (2013.01); *G01N 2291/02836* (2013.01)

(56) References Cited

U.S. PATENT DOCUMENTS

| | | |
|---|---|---|
| 2,340,992 A | 2/1944 | Siegel |
| 3,021,711 A | 2/1962 | Arvidson |
| 3,164,987 A | 1/1965 | Davidson |
| 3,218,851 A | 11/1965 | Anatole |
| 3,225,588 A | 12/1965 | Jacques |
| 3,648,512 A | 3/1972 | Abbotts |
| 3,677,067 A | 7/1972 | Miller et al. |
| 3,741,000 A | 6/1973 | Millerr |
| 3,763,692 A | 10/1973 | Agar |
| 3,955,401 A | 5/1976 | Catherall |
| 3,956,922 A | 5/1976 | November |
| 3,958,446 A | 5/1976 | November |
| 3,967,490 A | 7/1976 | Brady |
| 3,981,183 A | 9/1976 | Banks |
| 3,983,744 A | 10/1976 | Agar |
| 3,984,895 A | 10/1976 | Grice |
| 3,999,421 A | 12/1976 | Creswick |
| 4,007,627 A | 2/1977 | Stansfeld |
| 4,015,470 A | 4/1977 | Morrison |
| 4,020,330 A | 4/1977 | Du Bae |
| 4,023,400 A | 5/1977 | November |
| 4,024,759 A | 5/1977 | Klinger |
| 4,037,459 A | 7/1977 | Schlatter |
| 4,037,460 A | 7/1977 | November et al. |
| 4,037,461 A | 7/1977 | Miller |
| 4,041,769 A | 8/1977 | November |
| 4,063,448 A | 12/1977 | Agar |
| 4,064,738 A | 12/1977 | November |
| 4,064,739 A | 12/1977 | November et al. |
| 4,074,562 A | 2/1978 | North |
| 4,084,425 A | 4/1978 | Bae |
| 4,096,745 A | 6/1978 | Rivkin |
| 4,114,423 A | 9/1978 | Wenger |
| 4,117,716 A | 10/1978 | Simon |
| 4,127,028 A | 11/1978 | Cox |
| 4,129,031 A | 12/1978 | Tehon |
| 4,132,110 A | 1/1979 | Muramoto |
| 4,135,383 A | 1/1979 | November |
| 4,151,743 A | 5/1979 | Ghahramani |
| 4,158,959 A | 6/1979 | Blair |
| 4,170,128 A | 10/1979 | Kratky |
| 4,177,669 A | 12/1979 | Wenger |
| 4,187,721 A | 2/1980 | Smith |
| 4,192,184 A | 3/1980 | Cox |
| 4,193,291 A | 3/1980 | Lynnworth |
| 4,194,385 A | 3/1980 | November |
| 4,215,566 A | 8/1980 | Ghahramani |
| 4,217,774 A | 8/1980 | Agar |
| 4,232,544 A | 11/1980 | Stansfeld |
| 4,235,099 A | 11/1980 | Ishizaka |
| 4,240,285 A | 12/1980 | Langdon |
| 4,262,523 A | 4/1981 | Stansfeld |
| 4,265,125 A | 5/1981 | Mahany |
| 4,275,585 A | 6/1981 | Buzzell |
| 4,282,742 A | 8/1981 | Kalotay et al. |
| 4,283,936 A | 8/1981 | November |
| 4,297,608 A | 10/1981 | Jensen |
| 4,297,872 A | 11/1981 | Ikeda |
| 4,345,456 A | 8/1982 | Ponzi |
| 4,349,881 A | 9/1982 | November |
| 4,354,377 A | 10/1982 | Stansfeld |
| 4,361,052 A | 11/1982 | Nicol et al. |
| 4,362,048 A | 12/1982 | Agar |
| 4,411,161 A | 10/1983 | November |
| RE31,450 E | 11/1983 | Smith |
| 4,420,983 A | 12/1983 | Langdon |
| 4,429,564 A | 2/1984 | Ikeda |
| 4,442,700 A | 4/1984 | Swoboda |
| 4,445,389 A | 5/1984 | Potzick |
| 4,449,414 A | 5/1984 | Coates |
| 4,466,272 A | 8/1984 | Stansfeld |
| 4,470,294 A | 9/1984 | Hamel |
| 4,480,461 A | 11/1984 | Ponzi |
| 4,491,009 A | 1/1985 | Ruesch |
| 4,493,215 A | 1/1985 | Gast |
| 4,495,818 A | 1/1985 | Ikeda |
| 4,522,068 A | 6/1985 | Smith |
| 4,524,610 A | 6/1985 | Fitzgerald |
| 4,526,480 A | 7/1985 | Ward |
| 4,530,234 A | 7/1985 | Cullick |
| 4,546,641 A | 10/1985 | Nguyen |
| 4,550,768 A | 11/1985 | McMullen |
| 4,566,312 A | 1/1986 | Collins |
| 4,574,639 A | 3/1986 | Ward |
| 4,583,393 A | 4/1986 | Sweet |
| 4,601,200 A | 7/1986 | Stoffelen |
| 4,602,498 A | 7/1986 | Glikberg |
| 4,608,869 A | 9/1986 | Lerner |
| 4,614,115 A | 9/1986 | Pelletier |
| 4,624,129 A | 11/1986 | Haynes |
| 4,628,739 A | 12/1986 | Bruggen et al. |
| 4,640,128 A | 2/1987 | Lewis |
| 4,655,075 A | 4/1987 | Albert |
| 4,662,221 A | 5/1987 | Kaine |
| 4,671,099 A | 6/1987 | Lazarre |
| 4,674,322 A | 6/1987 | Stangeland |
| 4,677,842 A | 7/1987 | Piche |
| 4,679,947 A | 7/1987 | Miller |
| 4,683,752 A | 8/1987 | Bradshaw |
| 4,691,557 A | 9/1987 | Dunn |
| 4,754,640 A | 7/1988 | Fitzgerald |
| 4,770,042 A | 9/1988 | Cobb |
| 4,770,043 A | 9/1988 | Cobb |
| 4,783,987 A | 11/1988 | Hager |
| 4,788,466 A | 11/1988 | Paul |
| 4,796,468 A | 1/1989 | Blake-Coleman |
| 4,802,360 A | 2/1989 | Maier |
| 4,803,867 A | 2/1989 | Dahlin |
| 4,811,592 A | 3/1989 | Miura |
| 4,815,323 A | 3/1989 | Ellinger |
| 4,827,746 A | 5/1989 | Kawaguchi |
| 4,838,084 A | 6/1989 | Leopold |
| 4,848,139 A | 7/1989 | Blake-Coleman |
| 4,854,172 A | 8/1989 | Lemaster |
| 4,872,335 A | 10/1989 | Tsuruoka |
| 4,876,879 A | 10/1989 | Ruesch |
| 4,890,480 A | 1/1990 | Young |
| 4,893,496 A | 1/1990 | Bau |
| 4,905,499 A | 3/1990 | Miura |
| 4,909,068 A | 3/1990 | Miura |
| 4,912,962 A | 4/1990 | Kawaguchi |
| 4,922,745 A | 5/1990 | Rudkin |
| 4,934,177 A | 6/1990 | Cuthbertson |
| 4,958,332 A | 9/1990 | Tellerman |
| 4,959,228 A | 9/1990 | Skrgatic |
| 4,961,345 A | 10/1990 | Tsuruoka |
| 4,962,671 A | 10/1990 | Stansfeld |
| 4,991,124 A | 2/1991 | Kline |
| 4,996,656 A | 2/1991 | Hedrick |
| 4,996,871 A | 3/1991 | Romano |
| 5,000,050 A | 3/1991 | Hetrick |
| 5,005,400 A | 4/1991 | Lew |
| 5,025,656 A | 6/1991 | Wright |
| 5,048,323 A | 9/1991 | Stansfeld |
| 5,067,344 A | 11/1991 | Fitzgerald |
| 5,074,148 A | 12/1991 | Lew |

(56) References Cited

U.S. PATENT DOCUMENTS

| | | |
|---|---|---|
| 5,078,011 A | 1/1992 | Morkun |
| 5,117,146 A | 5/1992 | Martin |
| 5,157,962 A | 10/1992 | Fitzgerald |
| 5,201,215 A | 4/1993 | Granstaff |
| 5,214,955 A | 6/1993 | Yost |
| 5,218,858 A | 6/1993 | Jen |
| 5,237,853 A | 8/1993 | Cassaday |
| 5,253,522 A | 10/1993 | Nyce |
| 5,253,533 A | 10/1993 | Lam |
| 5,271,267 A | 12/1993 | Baumoel |
| 5,295,084 A | 3/1994 | Arunachalam |
| 5,323,638 A | 6/1994 | Langdon |
| 5,332,550 A | 7/1994 | Booker |
| 5,339,258 A | 8/1994 | Stabinger |
| 5,345,811 A | 9/1994 | Alexandrovich |
| 5,359,541 A | 10/1994 | Pope |
| 5,359,897 A | 11/1994 | Hamstead |
| 5,363,691 A | 11/1994 | Gallagher |
| 5,365,778 A | 11/1994 | Sheen |
| 5,383,349 A | 1/1995 | Blake-Coleman |
| 5,386,714 A | 2/1995 | Dames |
| 5,402,670 A | 4/1995 | Wicnienski |
| 5,471,873 A | 12/1995 | Nyce |
| 5,473,949 A | 12/1995 | Cage |
| 5,477,726 A | 12/1995 | Stabinger |
| 5,531,091 A | 7/1996 | Gademann et al. |
| 5,533,381 A | 7/1996 | Seale |
| 5,569,844 A | 10/1996 | Sowerby |
| 5,576,500 A | 11/1996 | Cage et al. |
| 5,606,113 A | 2/1997 | Sheen et al. |
| 5,670,709 A | 9/1997 | Gallagher |
| 5,675,071 A | 10/1997 | Cody |
| 5,687,100 A | 11/1997 | Buttler |
| 5,698,773 A | 12/1997 | Blom |
| 5,708,191 A | 1/1998 | Greenwood |
| 5,728,952 A | 3/1998 | Yao |
| 5,741,971 A | 4/1998 | Lacy |
| 5,753,327 A | 5/1998 | Cage |
| 5,804,698 A | 9/1998 | Belonenko |
| 5,814,739 A | 9/1998 | Van Cleve |
| 5,837,885 A | 11/1998 | Goodbread |
| 5,886,250 A | 3/1999 | Greenwood |
| 5,900,535 A | 5/1999 | Doe |
| 5,907,104 A | 5/1999 | Cage |
| 5,965,824 A | 10/1999 | Kishiro |
| 5,974,858 A | 11/1999 | Francisco |
| 5,987,966 A | 11/1999 | Fontanille |
| 5,996,225 A | 12/1999 | Ollila et al. |
| 6,006,589 A | 12/1999 | Rodahl |
| 6,029,501 A | 2/2000 | Nishino |
| 6,044,694 A | 4/2000 | Anderson |
| 6,050,141 A | 4/2000 | Tello |
| 6,073,495 A | 6/2000 | Stadler |
| 6,082,180 A | 7/2000 | Greenwood |
| 6,082,181 A | 7/2000 | Greenwood |
| 6,151,956 A | 11/2000 | Takahashi |
| 6,182,499 B1 | 2/2001 | McFarland |
| 6,189,367 B1 | 2/2001 | Smith |
| 6,247,354 B1 | 6/2001 | Vig |
| 6,269,686 B1 | 8/2001 | Hahn |
| 6,286,361 B1 | 9/2001 | Jones |
| 6,305,212 B1 | 10/2001 | Drzewiecki |
| 6,311,549 B1 | 11/2001 | Thundat |
| 6,314,791 B1 | 11/2001 | Rapp |
| 6,327,914 B1 | 12/2001 | Dutton |
| 6,336,353 B2 | 1/2002 | Matsiev |
| 6,360,606 B2 | 3/2002 | Hirota |
| 6,360,610 B1 | 3/2002 | Jarzynski |
| 6,370,939 B2 | 4/2002 | Smith |
| 6,389,877 B1 | 5/2002 | Takeuchi |
| 6,393,895 B1 | 5/2002 | Matsiev |
| 6,397,661 B1 | 6/2002 | Grimes |
| 6,401,519 B1 | 6/2002 | McFarland |
| 6,450,013 B1 | 9/2002 | Gallagher |
| 6,494,079 B1 | 12/2002 | Matsiev |
| 6,513,365 B1 | 2/2003 | Bruetting |
| 6,543,274 B1 | 4/2003 | Herrmann |
| 6,546,784 B2 | 4/2003 | Bilmes et al. |
| 6,557,416 B2 | 5/2003 | Chang |
| 6,634,214 B1 | 10/2003 | Thurston |
| 6,647,764 B1 | 11/2003 | Paul |
| 6,651,484 B2 | 11/2003 | Fiebelkorn |
| 6,684,683 B2 | 2/2004 | Potyrailo |
| 6,688,176 B2 | 2/2004 | Storm |
| 6,722,200 B2 | 4/2004 | Roukes |
| 6,732,570 B2 | 5/2004 | Francisco |
| 6,763,698 B2 | 7/2004 | Greenwood |
| 6,786,077 B2 | 9/2004 | Baumoel |
| 6,813,928 B2 | 11/2004 | Blakley |
| 6,826,949 B1 | 12/2004 | Berndt |
| 6,845,663 B2 | 1/2005 | Lopatin |
| 6,848,299 B2 | 2/2005 | Paul |
| 6,874,355 B2 | 4/2005 | Kornfeldt |
| 6,874,356 B2 | 4/2005 | Kornfeldt |
| 6,885,491 B2 | 4/2005 | Ross-Messemer |
| 6,904,786 B2 | 6/2005 | Matsiev |
| 6,912,904 B2 | 7/2005 | Storm |
| 6,918,283 B2 | 7/2005 | Berstis |
| 6,924,642 B1 | 8/2005 | Cho et al. |
| 6,928,877 B2 | 8/2005 | Carlson |
| 6,938,462 B2 | 9/2005 | Jakoby |
| 6,957,565 B2 | 10/2005 | Matsiev |
| 6,971,259 B2 | 12/2005 | Gysling |
| 6,986,276 B2 | 1/2006 | Gysling |
| 7,024,917 B2 | 4/2006 | DiFoggio |
| 7,059,169 B2 | 6/2006 | Cummings |
| 7,059,171 B2 | 6/2006 | Gysling |
| 7,059,172 B2 | 6/2006 | Gysling |
| 7,073,370 B2 | 7/2006 | Matsiev |
| 7,117,717 B2 | 10/2006 | Mattar |
| 7,134,320 B2 | 11/2006 | Gysling |
| 7,152,460 B2 | 12/2006 | Gysling |
| 7,191,638 B2 | 3/2007 | Lopatin |
| 7,216,543 B2 | 5/2007 | Paik |
| 7,254,987 B2 | 8/2007 | Tinianov et al. |
| 7,257,987 B2 | 8/2007 | O'Brien |
| 7,257,988 B2 | 8/2007 | Mattar et al. |
| 7,334,452 B2 | 2/2008 | Matsiev |
| 7,360,399 B2 | 4/2008 | Schmidt |
| 7,380,439 B2 | 6/2008 | Gysling |
| 7,399,609 B2 | 7/2008 | Lakshmi |
| 7,409,851 B2 | 8/2008 | Ilic |
| 7,426,866 B2 | 9/2008 | Van Tuyl |
| 7,437,909 B2 | 10/2008 | Wagner |
| 7,454,981 B2 | 11/2008 | Gysling |
| 7,523,640 B2 | 4/2009 | DiFoggio |
| 7,530,268 B2 | 5/2009 | Lopatin |
| 7,549,319 B2 | 6/2009 | Headrick |
| 7,552,619 B2 | 6/2009 | Andle |
| 7,562,557 B2 | 7/2009 | Bennett |
| 7,581,429 B2 | 9/2009 | Sparks et al. |
| 7,596,987 B2 | 10/2009 | Gysling |
| 7,597,008 B2 | 10/2009 | Patten |
| 7,610,795 B2 | 11/2009 | Bitto |
| 7,669,458 B2 | 3/2010 | Commuri |
| 7,689,370 B2 | 3/2010 | Grosser |
| 7,735,353 B2 | 6/2010 | Wagner |
| 7,788,979 B2 | 9/2010 | Vetelino |
| 7,831,400 B2 | 11/2010 | Stack |
| 7,874,199 B2 | 1/2011 | Chaudoreille |
| 7,878,044 B2 | 2/2011 | Andle |
| 7,908,903 B2 | 3/2011 | Wagner |
| 7,913,556 B2 | 3/2011 | Hsu |
| 7,921,691 B2 | 4/2011 | DiFoggio et al. |
| 7,941,284 B1 | 5/2011 | Glaudel |
| 7,958,772 B2 | 6/2011 | Permuy |
| 7,966,882 B2 | 6/2011 | Greenwood |
| 8,020,428 B2 | 9/2011 | Snieder |
| 8,087,284 B2 | 1/2012 | Babcock et al. |
| 8,166,801 B2 | 5/2012 | Sinha |
| 8,170,812 B2 | 5/2012 | Straub |
| 8,173,283 B2 | 5/2012 | Furukawa |
| 8,190,338 B2 | 5/2012 | Commuri |
| 8,215,170 B2 | 7/2012 | Tao |

(56) References Cited

U.S. PATENT DOCUMENTS

| | | |
|---|---|---|
| 8,281,646 B2 | 10/2012 | Waid et al. |
| 8,322,194 B2 | 12/2012 | Muller |
| 8,322,210 B2 | 12/2012 | Abele |
| 8,333,106 B2 | 12/2012 | Wagner |
| 8,408,045 B2 | 4/2013 | Forrer |
| 8,434,350 B2 | 5/2013 | Urban |
| 8,448,496 B2 | 5/2013 | Huang |
| 8,511,144 B2 | 8/2013 | Goravar |
| 8,601,857 B2 | 12/2013 | Ichihashi |
| 8,707,763 B2 | 4/2014 | Viachaslau |
| 9,429,458 B2 | 8/2016 | Hussain |
| 9,752,911 B2 * | 9/2017 | Cage ............... G01F 1/849 |
| 2002/0033054 A1 | 3/2002 | Frey et al. |
| 2003/0230150 A1 | 12/2003 | Drahm et al. |
| 2004/0000197 A1 | 1/2004 | Gysling |
| 2004/0226386 A1 | 11/2004 | Gysling et al. |
| 2006/0031030 A1 | 2/2006 | Bennett et al. |
| 2007/0186684 A1 | 8/2007 | Pham |
| 2007/0261407 A1 | 11/2007 | Bin-Nun et al. |
| 2010/0024569 A1 | 2/2010 | Ehrenberg et al. |
| 2010/0280757 A1 | 11/2010 | Agar et al. |
| 2011/0016988 A1 | 1/2011 | Tombs et al. |
| 2011/0023625 A1 | 2/2011 | Weinstein |
| 2011/0160893 A1 | 6/2011 | Rothman et al. |
| 2011/0199603 A1 | 8/2011 | Yoshioka et al. |
| 2016/0187176 A1 | 6/2016 | Cage |
| 2016/0187300 A1 | 6/2016 | Cage |
| 2016/0332129 A1 | 11/2016 | Cage |
| 2016/0334316 A1 | 11/2016 | Cage |

FOREIGN PATENT DOCUMENTS

| | | |
|---|---|---|
| JP | 2007-047071 | 2/2007 |
| JP | 2010-038752 | 2/2010 |
| WO | WO2006/107900 | 10/2006 |
| WO | WO2012/156980 | 11/2012 |
| WO | WO 2012030353 | 10/2014 |
| WO | WO 2014172111 | 10/2014 |

OTHER PUBLICATIONS

Written Opinion of the International Searching Authority for co-owned PCT patent application No. PCT/US2015/067716 dated Apr. 6, 2016, 10 pages.
Written Opinion of the International Searching Authority for co-owned PCT patent application No. PCT/US2016/32200 dated Aug. 16, 2016, 9 pages.
Written Opinion of the International Searching Authority for co-owned PCT patent application No. PCT/US2016/32204 dated Aug. 16, 2016, 11 pages.
Written Opinion of the International Searching Authority for co-owned PCT patent application No. PCT/US2015/067710, dated Jul. 13, 2017, 12 pages.
Written Opinion of the International Searching Authority for co-owned PCT patent application No. PCT/US2015/067716, dated Jul. 13, 2017, 12 pages.
PCT International Preliminary Report for PCT application No. PCT/US2016/032200, dated Aug. 16, 2016, 8 pages.
PCT International Preliminary Report for PCT application No. PCT/US2018/032204, dated Sep. 27, 2016, 8 pages.
English abstract for JP2007-047071 dated Feb. 22, 2007, 2 pages.
English abstract for JP2010-038752 dated Feb. 18, 2010, 2 pages.
International Search Report for PCT/US2015/067710, dated Apr. 6, 2016, 3 pages.
International Search Report for PCT/US2015/067716, dated Apr. 29, 2016, 3 pages.
Extended European Search Report, dated Jun. 22, 2018, 9 pages.

* cited by examiner

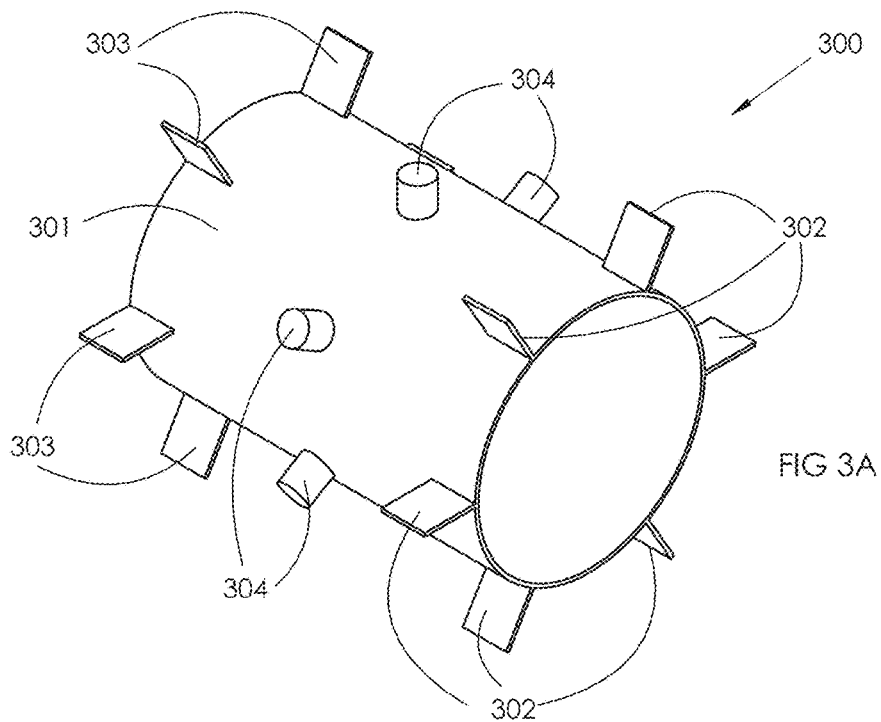
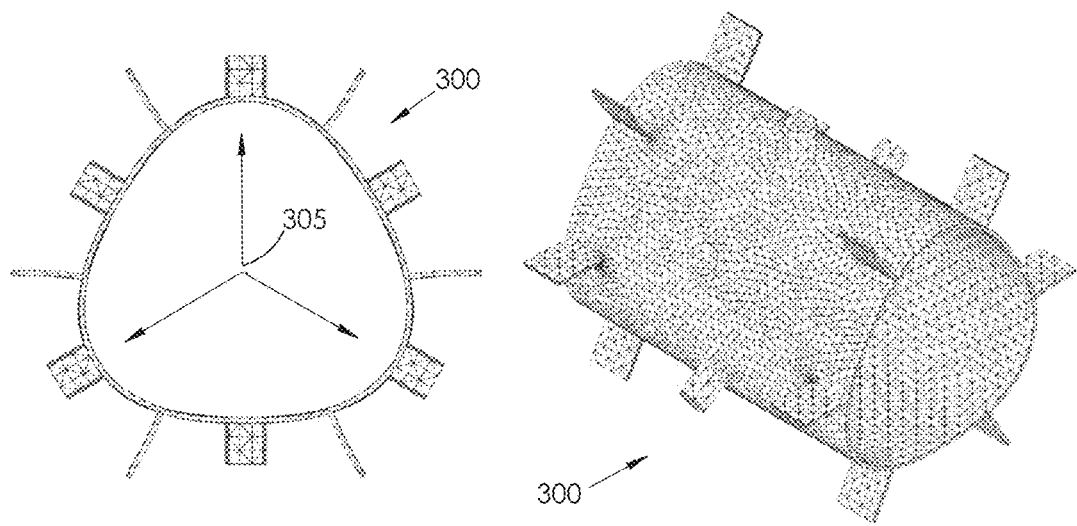
FIG 3A
FIG 3B
FIG 3C

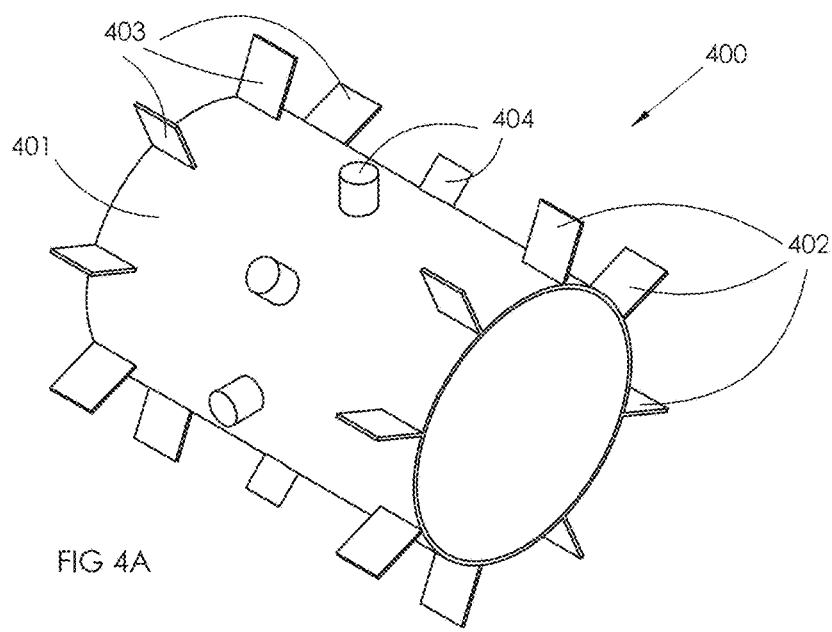
FIG 4A
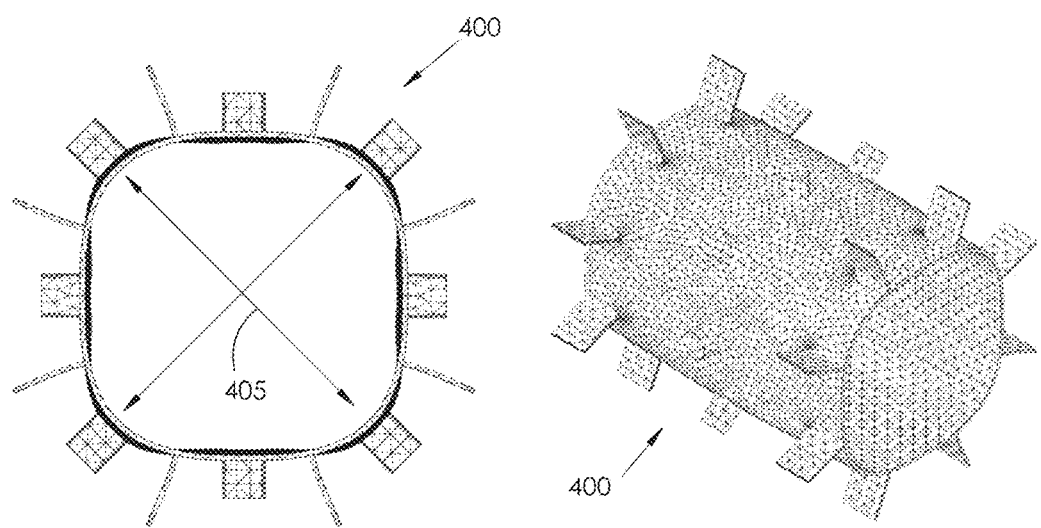
FIG 4B
FIG 4C

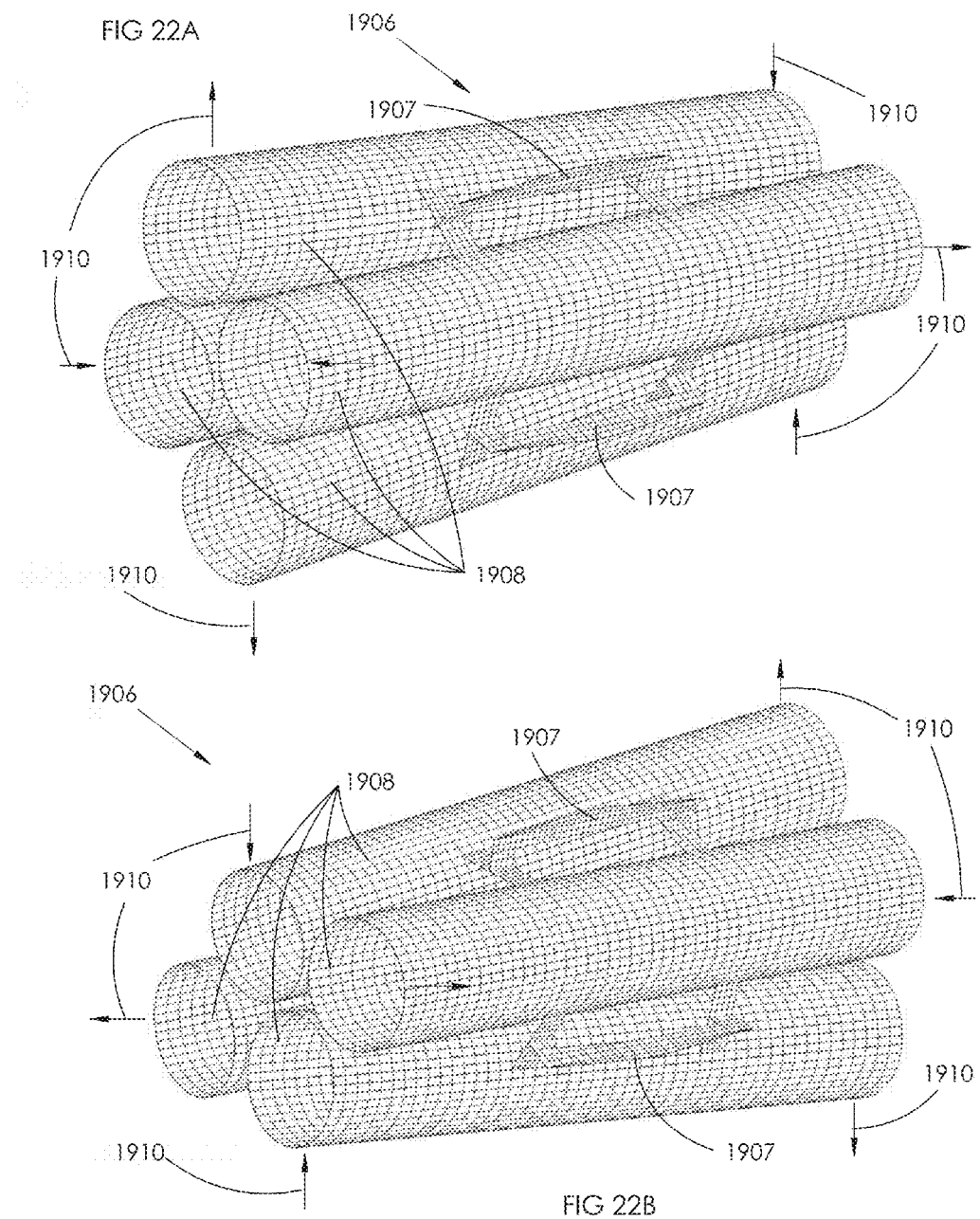

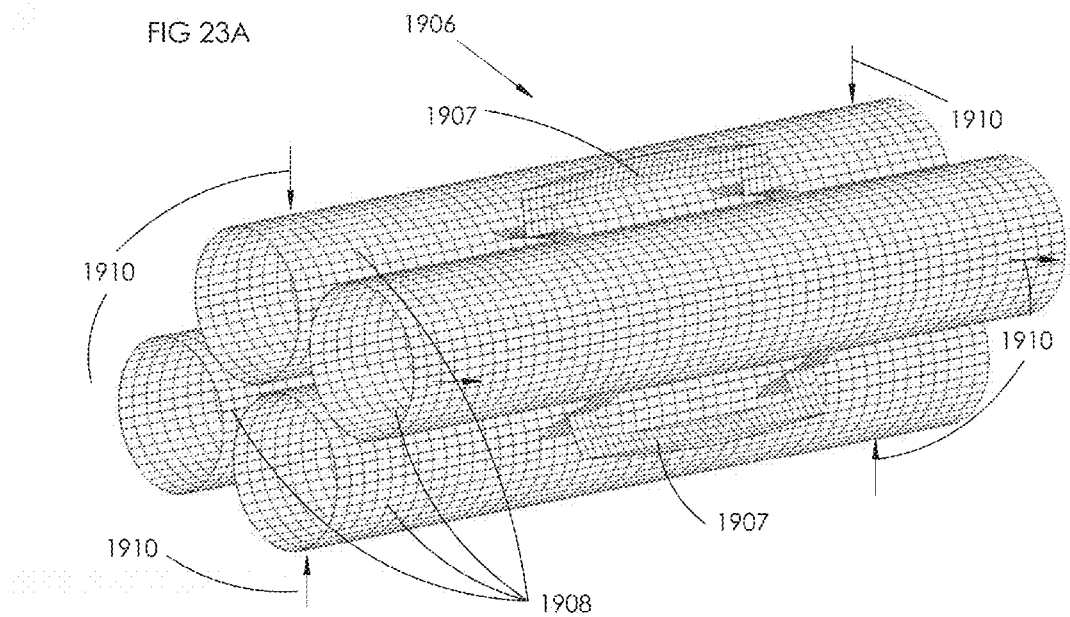
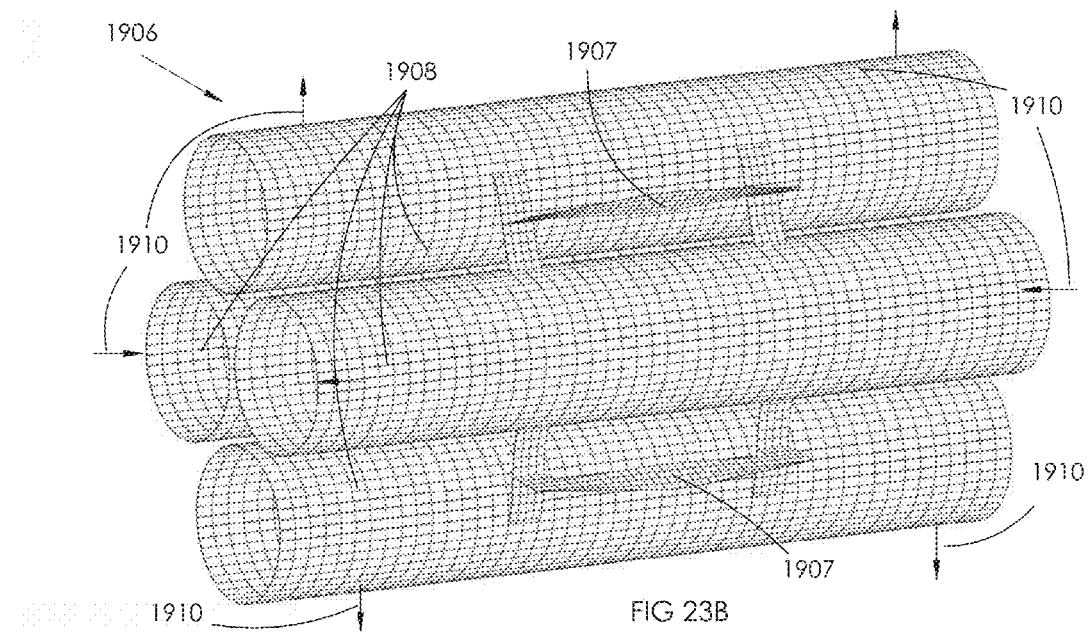

FLUID PARAMETER SENSOR AND METER

PRIORITY CLAIM AND CROSS REFERENCE

This application is a continuation-in-part (CIP) of U.S. patent application Ser. No. 14/981,272 filed Dec. 28, 2015 for "Fluid Parameter Sensor and Meter" of Donald R. Cage, et al., which claims the priority benefit of U.S. Provisional Patent Application No. 62/097,209 filed Dec. 29, 2014 for "A Vibrating Element Type Fluid Parameter Meter And Sensor For Abrasive Fluids" of Donald R. Cage, et al., each hereby incorporated by reference in its entirety as though fully set forth herein.

BACKGROUND

Meters for measuring fluid parameters generally have not been successful for abrasive fluids (e.g., fluids common in the hydraulic fracturing industry). These meters are often subject to premature failure and wear due to poor hydro-dynamic designs. Wear of the vibrating element also leads to a change in instrument calibration because the calibration factor is partly due to the geometry of the vibrating element, and abrasive wear changes the geometry. Traditional split-flow, and or bent tube type flow meters, densitometers and viscometers are examples of poor hydro-dynamic designs that are subject to failure and wear and calibration changes when used on abrasive fluids. Having a flow splitter or an elbow, or a bend or flange in the fluid path exacerbates wear caused by abrasive fluids because the abrasive particles in the fluid tend to scrape the outside of a curved path due to centrifugal forces.

BRIEF DESCRIPTION OF THE DRAWINGS

FIG. 3A is an isometric view of another example sensor element assembly having six mounting flexures at each end and six transducer magnets.

FIGS. 3B and 3C are two views of an example sensor element assembly shown as finite element analysis deflected shapes due to radial mode vibration.

FIG. 4A is an isometric view of another example sensor element assembly having eight mounting flexures at each end and eight transducer magnets.

FIGS. 4B and 4C are two views of an example sensor element assembly shown as finite element analysis deflected shapes due to radial mode vibration.

FIG. 10 is a close up cross section view of an example sensor element having a pattern where the openings are specifically shaped to induce fluid flow there through.

FIGS. 22A and 22B are two views of an example sensor element assembly shown as finite element analysis deflected shapes due to radial mode vibration.

FIGS. 23A and 23B are two views of an example sensor element assembly shown as finite element analysis deflected shapes due to radial mode vibration.

DETAILED DESCRIPTION

Figure 1A:
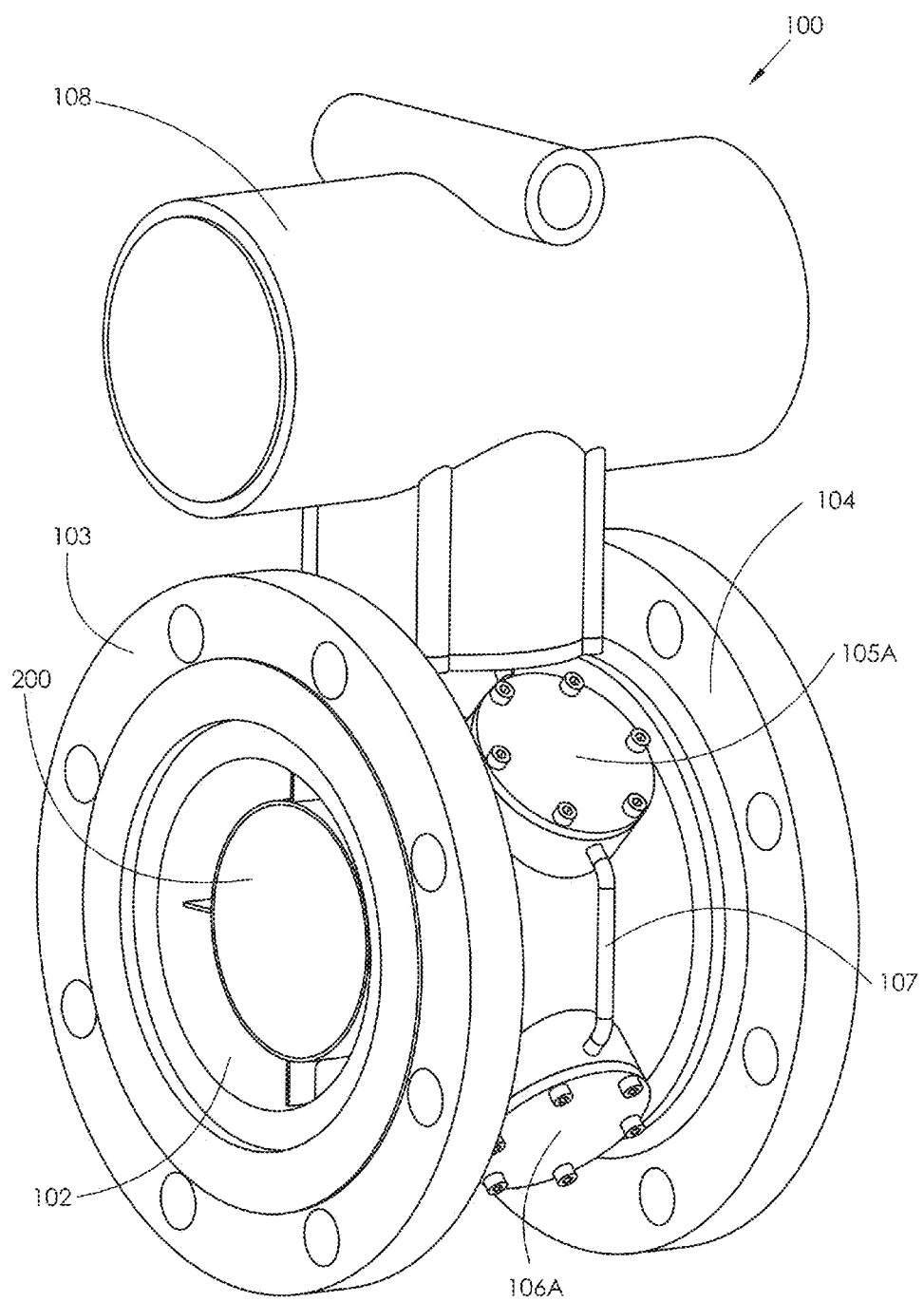
FIG. 1A is an isometric view of an example fluid parameter meter.

In the hydraulic fracturing industry, measurement of PPA ("Pounds of Propant Added") is important, and often employs nuclear densitometers having a radioactive source. However, these types of meters create a radiation exposure hazard to those nearby, and a national security risk should the equipment ever be lost or stolen. The United States Nuclear Regulatory Commission ("NRC") heavily regulates these devices because of the radioactive sources. Requisite reporting and security measures greatly increases the cost of ownership.

A fluid parameter meter is disclosed herein which may be employed, for example, in the hydraulic fracturing industry to eliminate the costs and concerns associated with current measurement devices. In an example, the fluid parameter meter includes a vibrating element type fluid parameter meter capable of measuring abrasive fluid parameters including fluid flow rate, fluid density, viscosity, temperature, and other parameters that can be calculated therefrom such as Reynolds Number, kinematic viscosity, mass flow rate, volume flow rate, net oil percentage, Gas volume fraction ("GVF"), and pounds of propant added ("PPA"), mass concentration, volume concentration, and others. The vibrating element is one or more uniform conduits fully immersed in the fluid to be measured and hydro-dynamically configured to minimize obstruction to the flow and to wear due to abrasive fluids such as hydraulic-fracturing ("fracking") fluids, oil well cementing fluids, slurries, and the like. Remote electromagnetic drivers and sensors are employed to cause and detect the requisite vibration from outside the fluid boundary, thereby allowing the vibrating element to freely vibrate without encumbrance. By isolating the vibrating element from the pressure and stress effects on the fluid boundary pipe, higher accuracy is achieved in a simple, robust, and wear resistant configuration.

In an example, the fluid parameter meter has a vibrating sensor element assembly comprised of one or more sensor elements, each having the shape of a straight uniform conduit, mounted within a straight section of outer conduit which bears the fluid pressure and pipeline stresses and vibrations. Each sensor element is a straight conduit, having a uniform and relatively small cross sectional area perpendicular to fluid flow direction, and having a central axis parallel to the fluid flow direction. One or more sensor element may be configured to vibrate in one or more natural radial type modes of vibration.

Radial modes of vibration have shapes that involve node areas having minimal vibration amplitude, and antinode areas having maximum vibration amplitude. In an example, attachment of the sensor element assembly into an outer conduit is accomplished with light springs (mounting flexures) attached at selected node or antinode areas, so that they do not substantially interfere with, or alter the natural radial mode shape of vibration that the sensor element assembly has vibrating freely by itself. These mounting flexures are also configured not to interfere with the fluid flow by minimizing their cross sectional area perpendicular to the fluid flow direction.

During operation, the sensor element assembly vibrates by electromagnetic transducers in one or more of its natural radial modes of vibration, at a prescribed amplitude and frequency, which induces fluid acceleration levels in the range of ten "g's" or less, and in an example, less than one "g".

In an example, the sensor element is a relatively thin walled round metal tube and is about one or two diameters long (although it may be more or less than this). The mounting flexures are metal fins having the approximate thickness of the wall of the sensor element. The mounting flexures connect between the outer conduit and the sensor element along the sensor element's vibrational node areas where vibration amplitudes are minimal.

By selecting thin walled sensor elements and mounting flexures relative to the diameter of the outer conduit, the flow area of the outer conduit may be ten to fifty times greater than the obstructed area of the sensor element and mounting flexures combined. With only about 2% to 10% of the flow area obstructed by sensor elements and mounting flexures, the measured fluids flow through the meter with little or no obstruction and pressure loss and wear. In addition, vibrating the fluid at acceleration levels (e.g., around ten "g's" or less, and in an example, less than one "g"), eliminates or minimizes induced cavitation and particle slippage induced wear.

In an example, the sensor element assembly is configured with a plurality of individual sensor element conduits arranged in parallel or series. As such, sensitivity to velocity profile effects can be minimized. An example is described herein with two uniform sensor element conduits of different diameters and arranged in parallel as a concentric pair. Another example is described herein having a plurality of smaller sensor element conduits arranged in parallel around a larger central sensor element. Still other examples are contemplated, as will be apparent to those having ordinary skill in the art after becoming familiar with the teachings herein.

Abrasive fluids flowing through the meter generally flow parallel to the vibrating walls of the sensor element and directly impinge on the leading edges of the sensor element and mounting flexures. The sensor elements and mounting flexures can therefore be protected from wear by manufacture of abrasion resistant materials (e.g., abrasion resistant or hardened steel, or ceramic, or polymer). In addition, the leading edges can be further protected by hardening, or by coating, or by a wear guard mounted upstream from the sensor element assembly.

Several sensor element examples are described herein having various cross sectional shapes and various arrangements of mounting flexures and drive and sense magnets to enable vibration of various natural modes of vibration. In addition, example sensor elements are described herein having patterns of openings holes or slots to enable fluid flow through the wall of the sensor element to modify meter measurement sensitivity, minimize wall effects, and minimize power consumption. Also described are openings or holes in the sensor element that are specifically shaped to induce flow between the sensor element interior and exterior surfaces.

The fluid parameter meter disclosed herein can be provided as a sensor, or as a complete meter or system, because the sensors are often manufactured and sold separately from controlling electronics or complete meters. Therefore, the description of the fluid parameter meter herein is not limited in application, and applies to both sensors and meters or systems.

Before continuing, it is noted that as used herein, a complete "meter" may be referred to as a combination of a "sensor" and its controlling "electronics" The sensor may be defined as the mechanical portion of a meter including, but not limited to, a flow conduit pipe, sensor element tubes, magnets, coils, armatures, temperature sensors, mounting flexures, flanges and the like. The electronics may be defined as that portion of a complete meter that receives and sends electrical signals to the sensor, and processes those signals for various control and parameter determinations.

It is also noted that the terms "hole" or "holes" and "opening" or "openings" are used interchangeably herein.

In addition, the terms "includes" and "including" mean, but not limited to, "includes" or "including" and "includes at least" or "including at least." The term "based on" means "based on" and "based at least in part on."

Figure 1B:
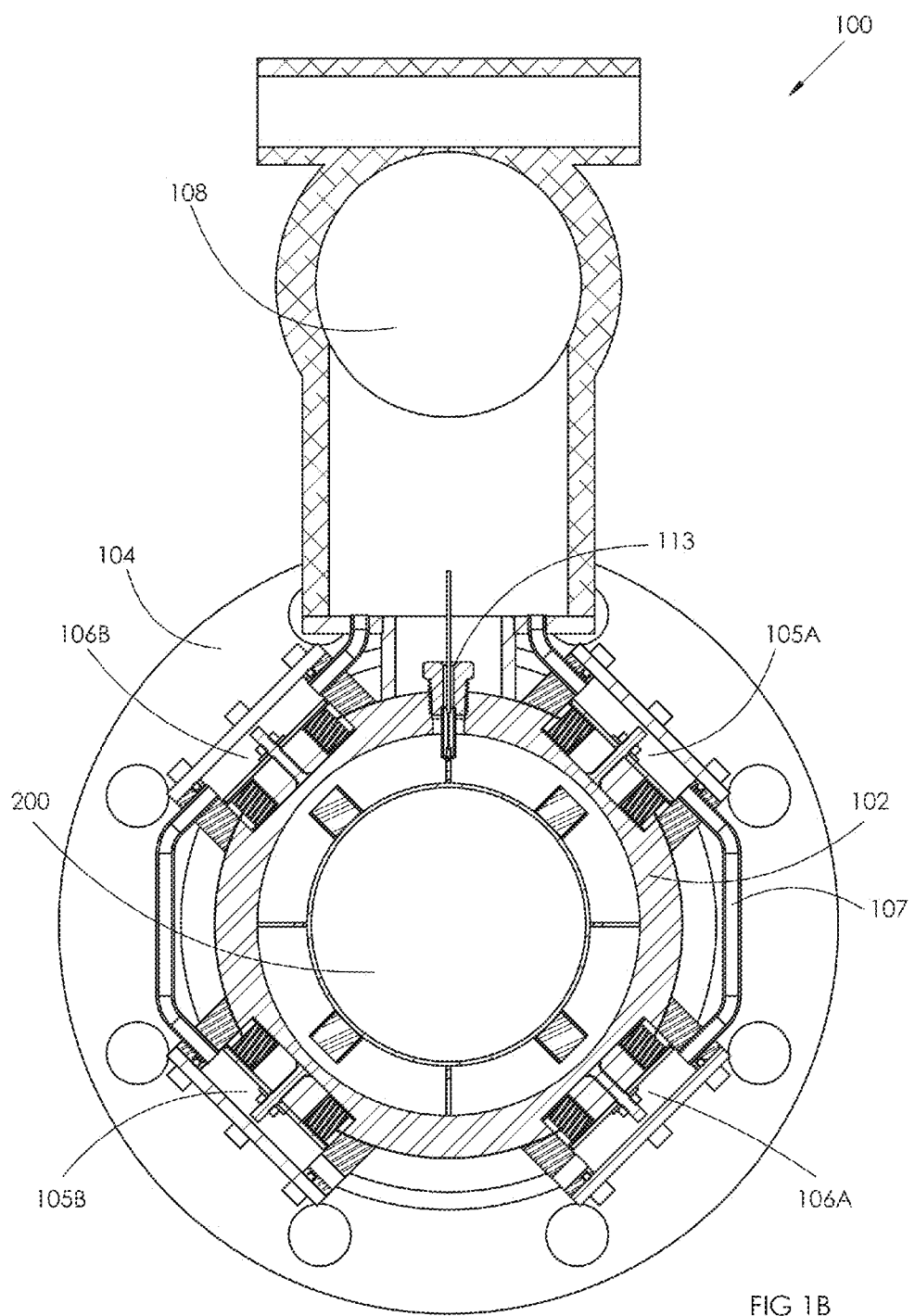
FIG. 1B is a cross section view looking down the central fluid flow axis of the example fluid parameter meter of FIG. 1A.
Figure 1C:
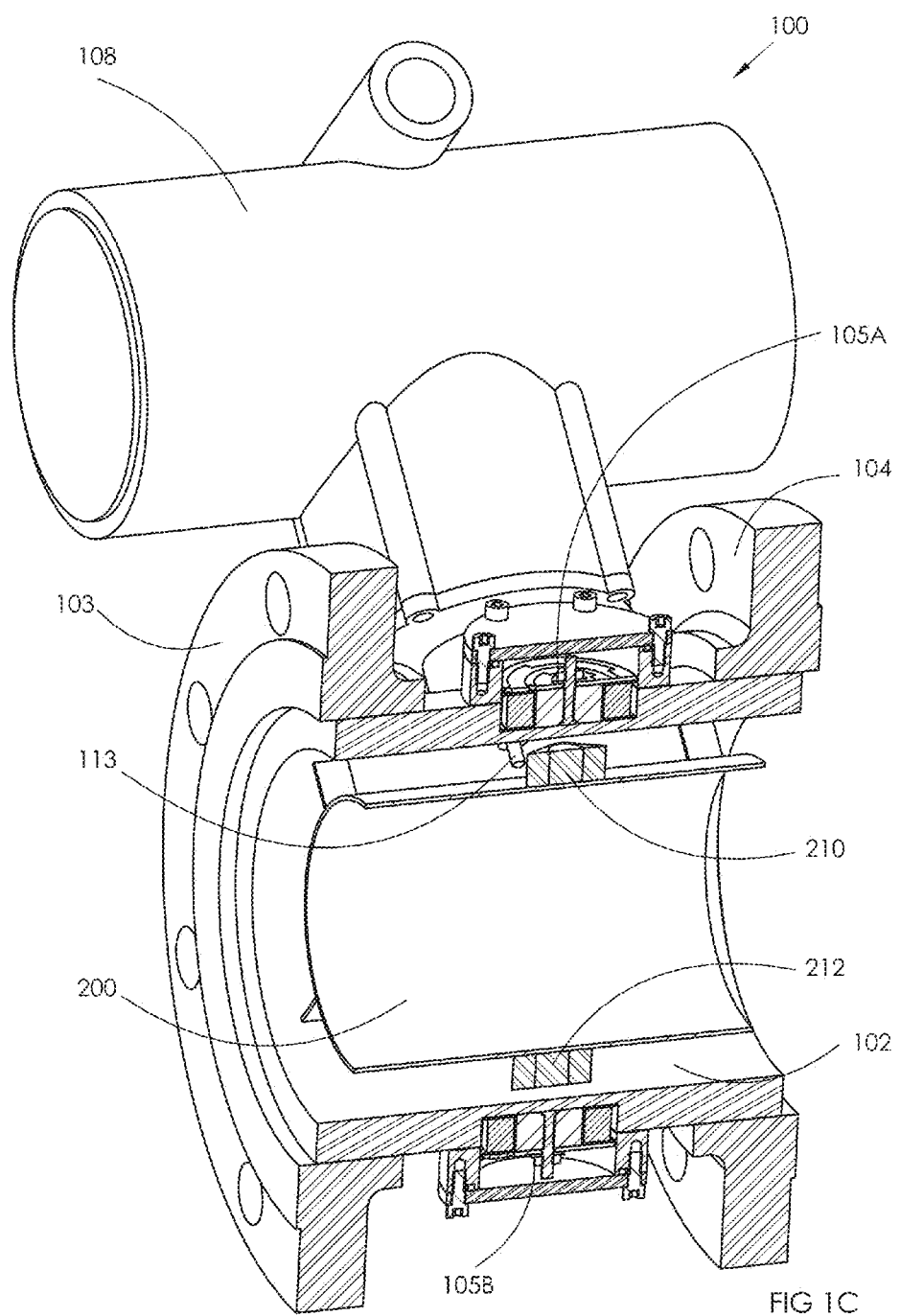
FIG. 1C is an oblique cross section view of the example fluid parameter meter of FIG. 1A.
Figure 1D:
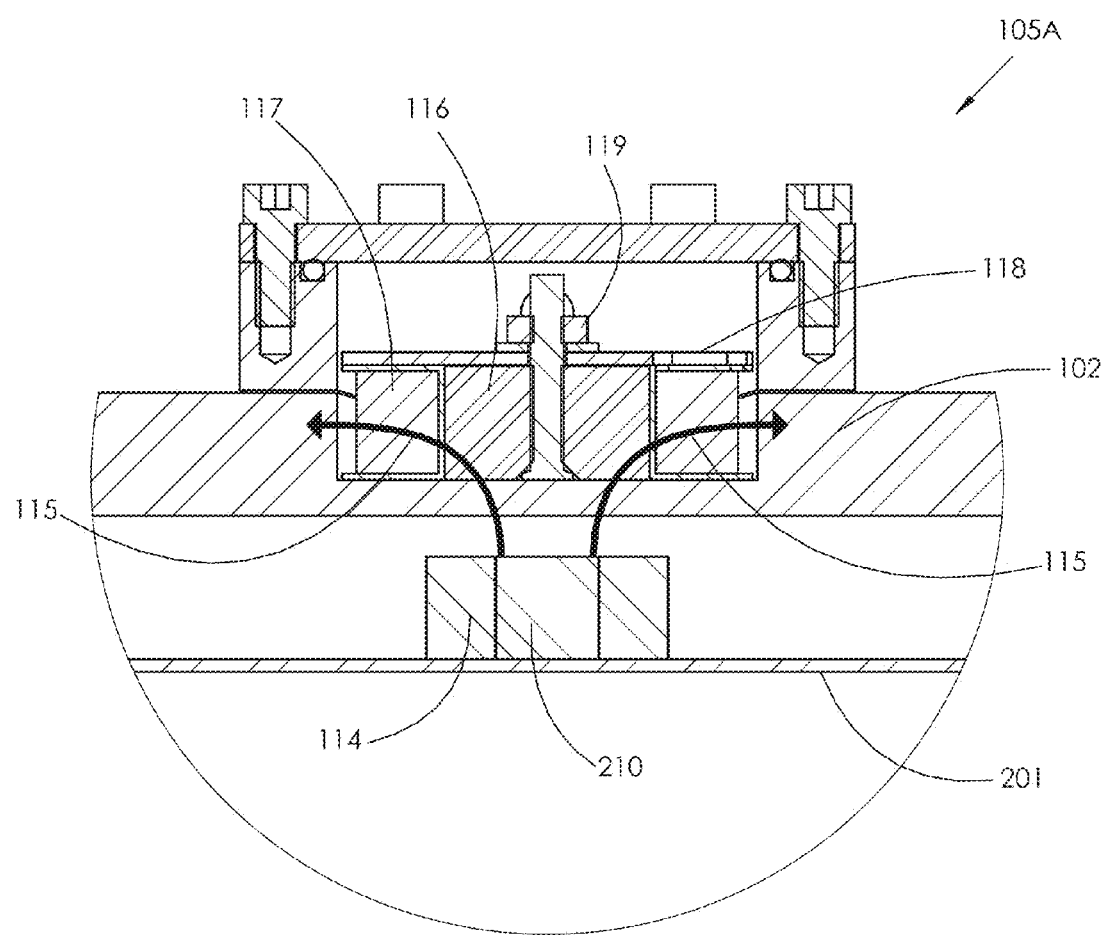
FIG. 1D is a close up view of the example electromagnetic driver shown in FIG. 1C.
Figure 2A:
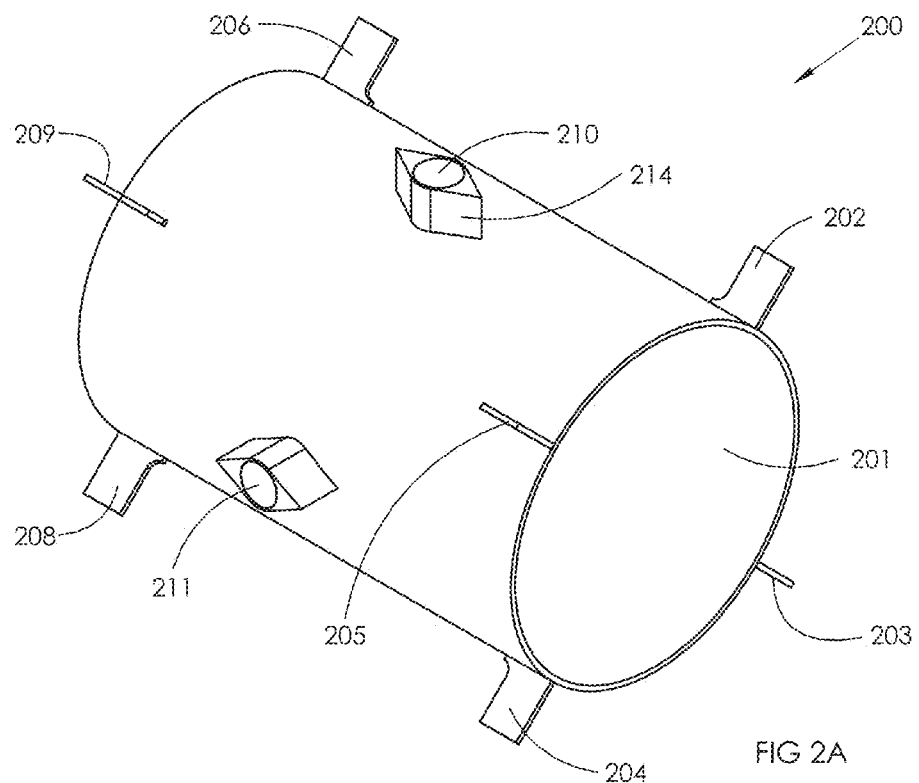
FIG. 2A is an isometric view of an example sensor element assembly.
Figure 2B:
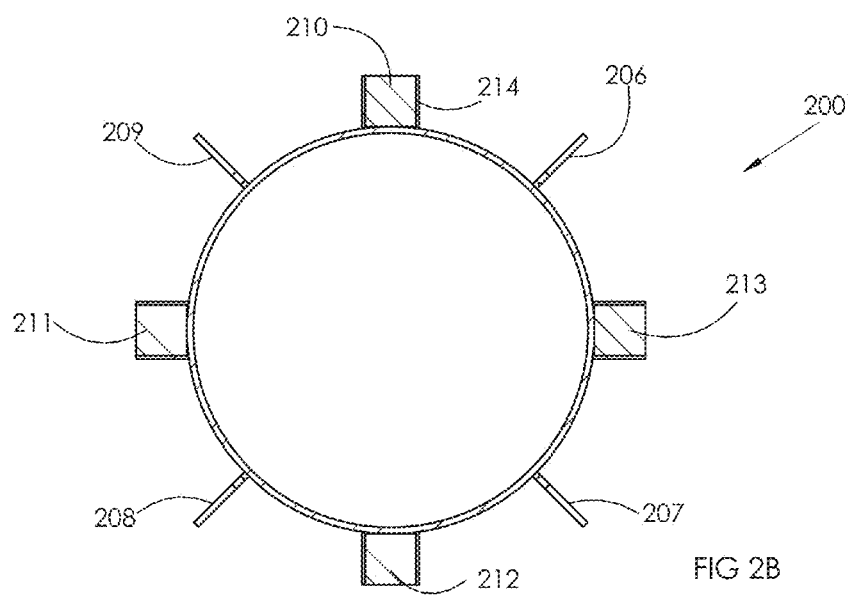
FIG. 2B is a cross section view looking down the central fluid flow axis of the example sensor element assembly shown in FIG. 2A.
Figure 2C:
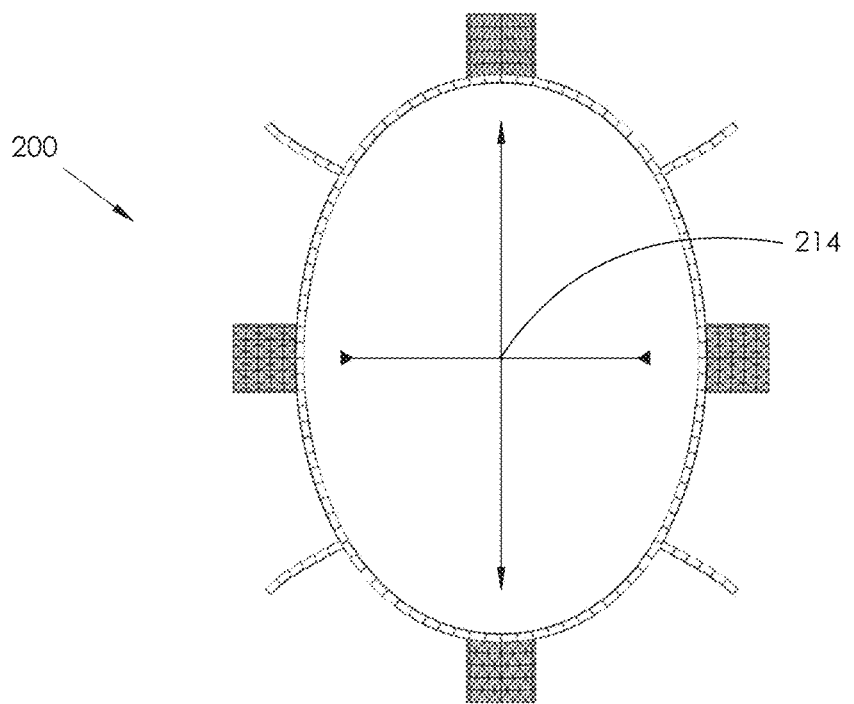
FIGS. 2C and 2D are two views of an example sensor element assembly shown as finite element analysis deflected shapes due to radial mode vibration.
Figure 2D:
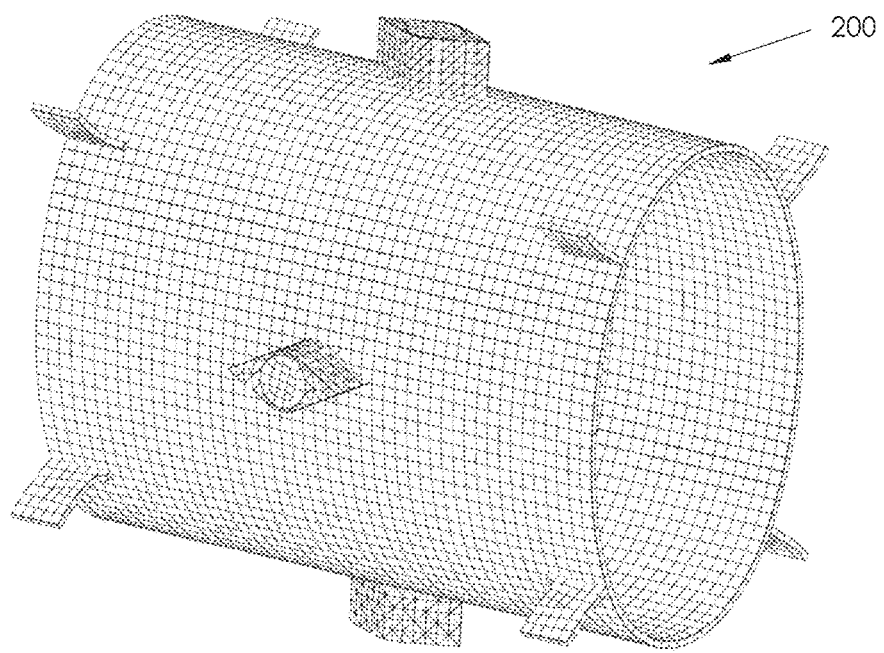

FIG. 1A is an isometric view of an example fluid parameter meter 100. FIG. 1B is a cross section view looking down the central fluid flow axis of the example fluid parameter meter 100 of FIG. 1A. FIG. 1C is an oblique cross section view of the example fluid parameter meter 100 of FIG. 1A. FIG. 1D is a close up view of the example electromagnetic driver shown in FIG. 1C. FIG. 2A is an isometric view of an example sensor element assembly 200. FIG. 2B is a cross section view looking down the central fluid flow axis of the example sensor element assembly 200 shown in FIG. 2A. FIGS. 2C and 2D are two views of an example sensor element assembly 200 shown as finite element analysis deflected shapes due to radial mode vibration.

An example fluid parameter meter 100 includes flanges 103 and 104 which, and for this example are standard 6 inch 150 pound ANSI pipe flanges. Flanges 103 and 104 are welded to outer conduit 102 which is a 6 inch pipe. Also mounted in association with the outside of outer conduit 102 is electronics housing 108 which holds the control electronics 1401 through 1405 for meter 100. Also mounted in association with outer conduit 102 are magnet-coil assemblies 105A and 105B, and 106A and 106B, and wire conduits 107 for conveying electrical wires.

In an example, a temperature sensor 113 is mounted in association with outer conduit 102. The temperature sensor may be a platinum RTD (resistive thermal device) in a thermal well arrangement for determining fluid temperature in a pipe. Temperature sensor 113 is configured to acquire an accurate temperature of any fluid inside of outer conduit 102. In an example, temperature sensor 113 may be provided for reporting fluid temperature to the meter user, and for compensating for temperature related material property changes in sensor element assembly 200.

In an example, sensor element assembly 200 is mounted inside of outer conduit 102, as shown in detail in FIGS. 2A and 2D. Sensor element assembly 200 is comprised of sensor element 201 which is a round steel tube of 4 inch diameter, 0.06 inch wall thickness, and 6 inches long. Mounting flexures 202 through 205 are also made of steel in the shape of thin walled flexural fins approximately 0.5 inches by 0.6 inches by 0.06 inches thick, and are mounted by brazing or welding toward the lower right (proximal) end of sensor element 201 of FIG. 2A, and along the sides of sensor element 201 on minimum vibration nodes. Mounting flexures 202 through 205 are aligned at 45, 135, 225, and 315 degrees respectively, around the circumference of sensor element 201. Toward the opposite (distal) end of sensor element 201 are mounting flexures 206 through 209 (not all mounting flexures are visible in all views) which are similar to and aligned with mounting flexures 202 through 205 respectively.

In an example, the sensor element assembly 200 has four permanent magnets 210 through 213, fixedly attached to the side of sensor element 201 about half way along its length, and at the peak displacement locations (antinodes) for the mode of vibration (not all magnets are visible in all views). By way of illustration, magnets 210 through 213 may be samarium cobalt type magnets due to their strength and temperature stability. In another example, neodymium iron, alnico, or other magnetic materials may be provided. Still other magnets may be provided. Permanent magnets 210 through 213 are aligned at 0, 90, 180 and 270 degrees respectively, around the circumference of sensor element 201. Permanent magnets 210 through 213 can be interchangeably provided for either causing requisite vibration, or for sensing the vibration thus caused as further explained hereinafter.

In an example, sensor element 201 is a short straight section of relatively thin walled uniform tubing made of metal such as a corrosion resistant 300 series stainless steel, or a hardened type of metal such as 410 stainless steel, or PH 17-4, or 4340 steel. Non-metals can also be provided for this purpose such as ceramics, plastics, reinforced polymers, reinforced polyphenylene-sulfide, glass filled nylon, and the like. The length of sensor element 201 may be selected depending on desired vibration characteristics. In an example, the length is generally about one or two diameters in length or shorter, and circular in cross sectional shape. FIG. 7A through 7D show other example cross sectional shapes for sensor elements including octagonal 701, hexagonal 702, multi-lobed shaped 703, or elliptical 704. In an example, outer conduit 102 may be a round stainless steel pipe, although other shapes may also be implemented.

FIG. 1D shows a close up cross section view of magnet-coil assembly 105A. Magnet-coil assembly 105A is comprised of permanent magnet 210 which is fixedly attached to and moves with the vibration of sensor element 201, and is protected from abrasive fluids by magnet guard 114 which may be made of a hard abrasive resistant material such as 410, 440, or 17-4 type stainless steel. Magnet guard 114 can be a simple tubular sleeve, but may also be a more hydrodynamic configuration as shown, and such as magnet guard 906 of FIG. 9A. Permanent magnet 210 causes magnetic field 115 to emanate therefrom, and pass through the wall of outer conduit 102, through armature 116, and through electrical coil 117. Electrical coil 117 is held in place by an interconnecting printed circuit board 118 and by fastener 119. In an example, armature 116 enhances the magnitude and direction of magnetic field 115, for example, if it is made of a magnetically permeable material such as carbon steel or 400-series stainless steel or the like.

In an example, magnet coil assemblies 105A, 105B, 106A, and 106B are all constructed in the same way as just described for magnet coil assembly 105A, therefore each magnet coil assembly can be provided either as a vibration driver or as a vibration sensor and are therefore interchangeable. As the mode of vibration for this example causes elliptical deflections of the sensor element 201 cross sectional shape as shown in FIGS. 2C and 2D, diametrically opposite magnet coil assemblies can be electrically connected together to work as a pair. Thus, magnet coil assemblies 105A and 105B are electrically connected and work as one vibration sensor as shown in electrical schematic 1400 of FIG. 14 where electrical signals from magnet coil pair 105A and 105B supply a vibration related signal to amplifier 1401. Similarly, magnet coil assemblies 106A and 106E can be electrically connected as a pair and work as one vibration driver as shown in FIG. 14 where amplifier 1402 supplies electrical excitation to magnet coil assemblies 106A and 106B.

Figure 14:
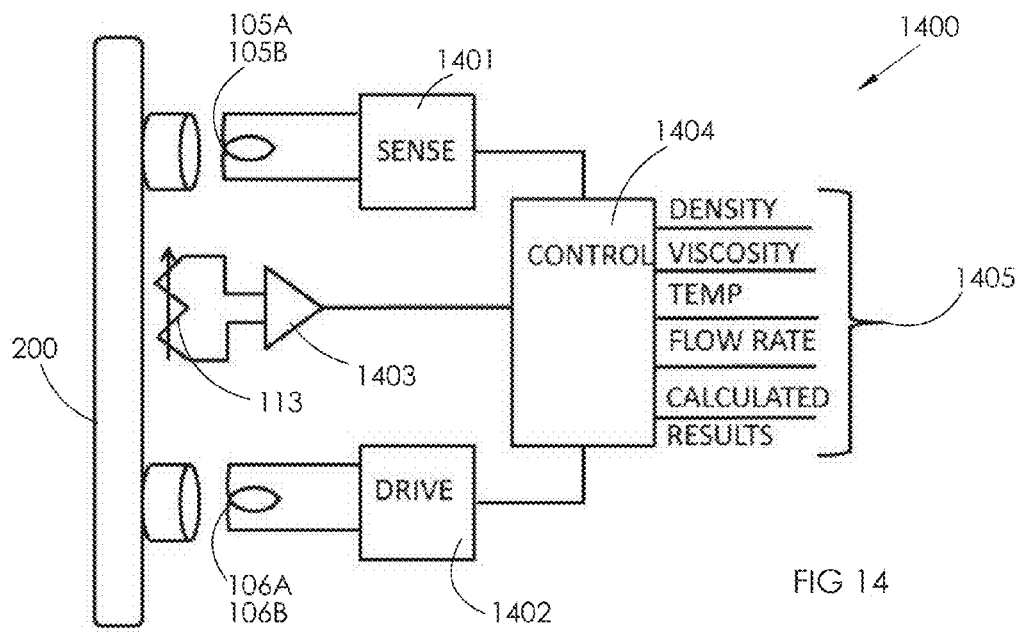
FIG. 14 is a block diagram showing signal processing for an example fluid parameter meter.

FIG. 14 also shows control module 1404 which receives vibration signals from amplifier 1401, and thereby controls amplifier 1402 to supply the requisite vibration forces to maintain a prescribed vibration mode and amplitude. Temperature Sensor 113 is also represented in electrical schematic 1400 and is also connected to control module 1404 via amplifier 1403 to deliver fluid temperature related signals thereto.

During operation, control module 1404 uses vibration signals and temperature signals to determine output fluid parameters 1405 such as fluid density, viscosity, temperature, and other calculated results such as net percentage oil, pounds of propant added, gas volume fraction, or others. The determination of these calculated results may also involve user input or assumed values such as water density, propant density, or others.

An example method of vibrating the sensor element assembly is now briefly described. Ambient vibration on sensor element assembly 200 causes an electrical signal in magnet coil assemblies 105A and 105B which is amplified by amplifier 1401 and passed along to control module 1404. Control module 1404 creates an output signal related to the vibration that is detected by magnet coil assemblies 105A and 105B. This output signal, usually a sine wave, is amplified by amplifier 1402 and converted to a current of the appropriate phase and amplitude to reinforce the vibration just detected. The current thus created passes through magnet coil assemblies 106A and 106B thereby causing forces on sensor element assembly 200 to reinforce the desired vibration shape 214. By reinforcing the detected vibration in this way, the amplitude of the vibration shape 214 on sensor element assembly 200 may increase until it reaches a specified amplitude as determined by control module 1404. Once the specified amplitude is achieved, the amplification from amplifier 1402 is reduced to a level to maintain the specified vibration shape 214 amplitude. This vibration amplitude is maintained during normal operation and while the desired fluid parameters are determined.

Figure 13:
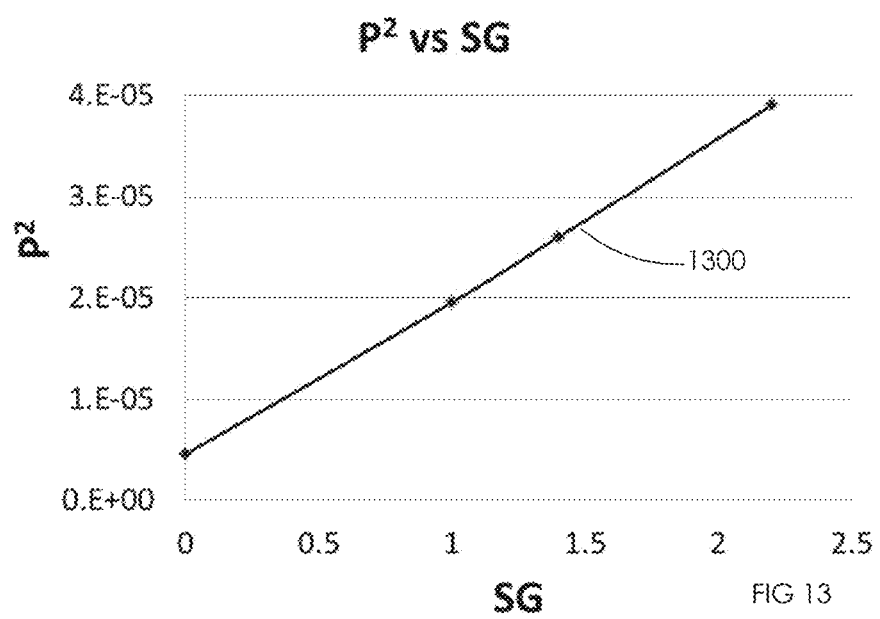
FIG. 13 is a graph illustrating a relationship between vibration period squared versus fluid specific gravity for an example fluid parameter meter, to determine fluid density from vibration period.

To determine fluid density in an example, the period of oscillation is determined and squared by control module 1404. The period squared value is a representation of fluid density or specific gravity. FIG. 13 is graph 1300 of four different fluid specific gravities, plotted against their vibration period squared value. Graph 1300 shows a general linear relationship between vibration period squared and fluid specific gravity. This graph 1300 can therefore be reduced to an equation for control module 1404 to calculate any fluid's specific gravity based on the vibration period. Normally each meter is calibrated at the factory to determine the equation of graph 1300 by testing the meter on two or more fluids such as air and water. The equation to calculate fluid density based on vibration period can also involve compensation values based on temperature and viscosity or others.

To determine fluid viscosity in an example, the power or force to maintain a prescribed level, or velocity, or amplitude of vibration is determined by control module 1404 as a representation of fluid viscosity. As an example, the force to cause sensor element vibration, divided by the velocity of the resulting vibration is proportionally related to fluid damping or viscosity.

To determine temperature in an example, the RTD 113 is normally a platinum type thin film or wire wound type sensor and circuit module 1403 is a commercial integrated circuit that supplies RTD 113 with a small current and measures the resistance of the RTD and converts that resistance to a temperature signal which is supplied to control module 1404. This is accomplished by application of the Callendar Van Dusen equation and there are many commercially available electronic modules available for this purpose.

To determine the calculated result of PPA ("pounds of propant added") in an example, the fluid density is determined by the method earlier described. Using a user supplied density of the propant, and a user supplied or assumed density of the fluid mixed with the propant, the PPA can thereby be determined as a function of the two known densities, and the measured density of the mixed fluid in the meter.

Similarly, the percentage of oil in a mixture of water and oil "net oil" can be determined. Providing a user specified or an assumed density for the water portion of the mixture, the net-oil percentage can be determined in an example, as a function of the measured density of the mixture, and the user specified or assumed density of the water.

Similarly, gas volume fraction ("GVF") of a mixture of gas and fluid can be determined. Using a user specified or an assumed density for the fluid portion of the mixture, the GVF can be determined in an example, as a function of the measured density of the mixture, and the user specified or assumed density of the fluid.

Following is an example for a sensor element assembly 200 along with density test results. In this example, Sensor Element 201 is 6" long, 4" diameter, 0.06" wall thickness, 316 SS. The Mounting Flexures are 202-209: 0.5" wide, 0.6" tall, 0.06" thick, 316 SS. The Magnets are 210-213: 0.5" diameter 0.5" long, Samarium Cobalt. Density Results are plotted in FIG. 13, line 1300 and show a linear relationship between fluid specific gravity (SG) and vibration period squared (VP^2). Test results are shown in Table 1.

| Fluid | SG | Frequency (Hz) | VP^2 |
|---|---|---|---|
| Air | 0.001 | 465 | 4.62e−6 |
| Water | 1.00 | 226 | 1.96e−5 |
| Fracking Fluid | 1.4 | 196 | 2.6e−5 |
| Zinc Bromide | 2.2 | 160 | 3.9e−5 |

In an example, the amplitude of vibration shape 215 to accurately detect and drive the vibration frequency on water can be 0.0002" or less. Acceleration equals amplitude times circular frequency squared. Therefore, the acceleration level for this example on water is given by the following equation:

$$\text{Acceleration} = 0.0002 * (2*pi*226)^2 = 403 \text{ in/sec/sec} \qquad \text{EQ 1:}$$

The result is slightly more than one "g" of acceleration. This low acceleration level eliminates or minimizes induced cavitation and particle slippage problems.

Before continuing, it should be noted that the examples described above are provided for purposes of illustration, and are not intended to be limiting. Other devices and/or device configurations may be utilized to carry out the operations described herein.

FIG. 3A is an isometric view of another example sensor element assembly 300 having six mounting flexures at each end and six transducer magnets. FIGS. 3B and 3C are two views of an example sensor element assembly 300 shown as finite element analysis deflected shapes due to radial mode vibration.

FIG. 3A is another example sensor element assembly 300. Sensor element assembly 300 is similar to sensor element assembly 200 except that instead of having 4 mounting flexures at each end of the sensor element assembly 200, sensor element assembly 300 has six mounting flexures 302 and 303 at each end, and 6 magnets 304 at the mid length position. Having six mounting flexures at each end 302 and 303, and six magnets 304 allows sensor element assembly 300 to vibrate in a higher order mode of vibration where the cross section vibration shape 305 is more triangular as shown in FIGS. 3B and 3C. In an example, the vibration shape 305 is uniform along the length of sensor element assembly 300.

The operation of sensor element assembly 300 is similar to that of sensor element assembly 200 earlier described, except that six magnets 304 are provided for driving and sensing the vibration motion 305, three for driving and three for sensing the vibration motion 305. In this example, three magnets 304 are provided for driving and three magnets 304 are provided for sensing so that the driving forces are balanced. It is noted however, that other combinations of driving and sensing magnets may be provided.

FIG. 4A is an isometric view of another example sensor element assembly 400 having eight mounting flexures at each end and eight transducer magnets. FIGS. 4B and 4C are two views of an example sensor element assembly 400 shown as finite element analysis deflected shapes due to radial mode vibration.

FIG. 4A is another example sensor element assembly 400. Sensor element assembly 400 is similar to sensor element assembly 300, except that instead of having six mounting flexures at each end of the sensor element assembly 300. Sensor element assembly 400 has eight mounting flexures 402 and 403 at each end, and 8 magnets 404 at the mid length position. Having eight mounting flexures 402 and 403, and eight magnets 404 allows sensor element assembly 400 to vibrate in a higher mode of vibration where the cross section vibration shape 405 is more rectangular as shown in FIGS. 4B and 4C. In an example, the vibration shape 405 is uniform along the length of sensor element assembly 300.

The operation of sensor element assembly 400 is similar to that of sensor element assembly 200 earlier described, except that eight magnets 404 are provided for driving and sensing the vibration motion 405, four for driving and four for sensing the vibration motion 405. In this example, four magnets 404 are provided for driving and four magnets 404 are provided for sensing so that the driving forces are balanced. It is noted, however, that other combinations of driving and sensing magnets may be provided.

Figure 5A:
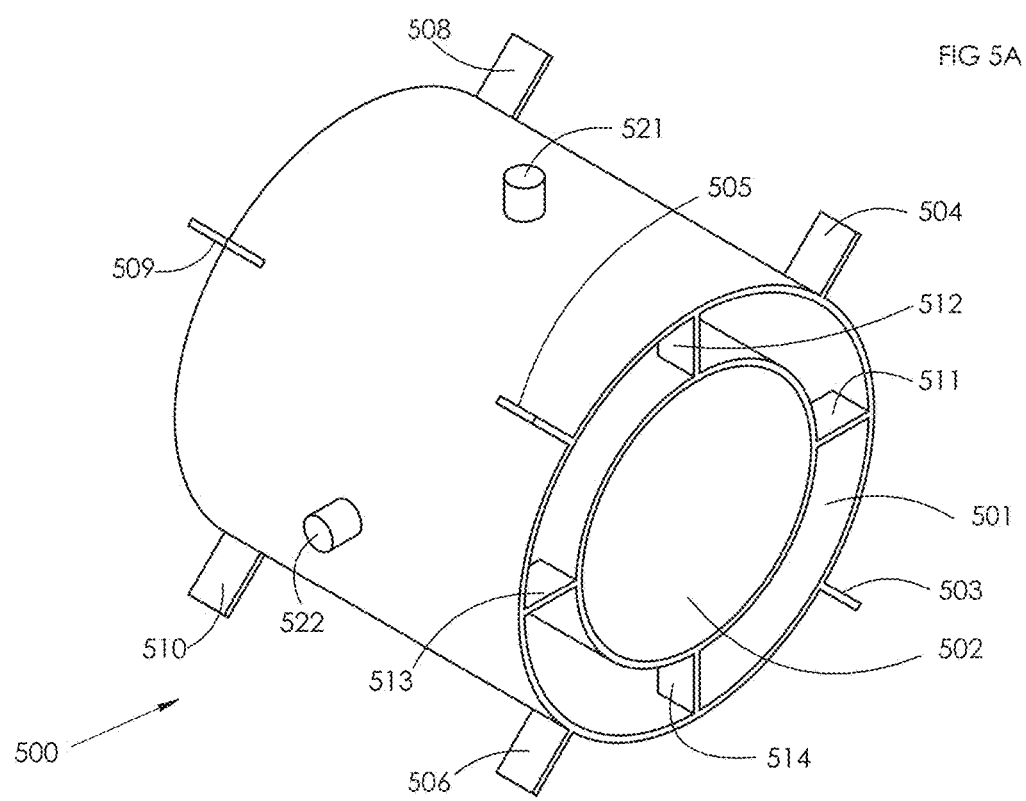
FIG. 5A is an isometric view of another example fluid parameter meter, where the sensor element assembly has two sensor element conduits arranged in parallel as a concentric pair.
Figure 5B:
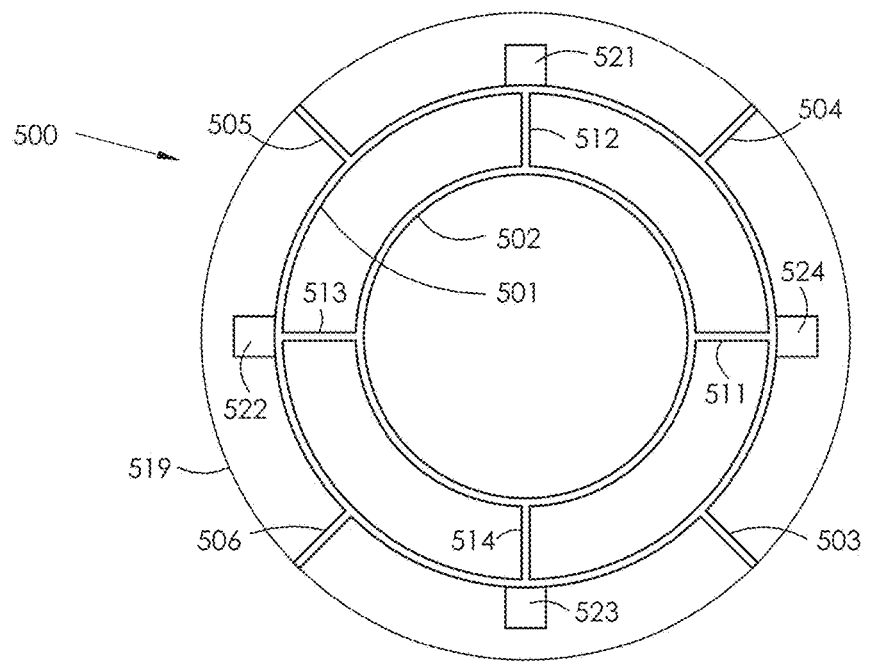
FIG. 5B is a view down the central fluid flow axis of the example fluid parameter meter shown in FIG. 5A.
Figure 5C:
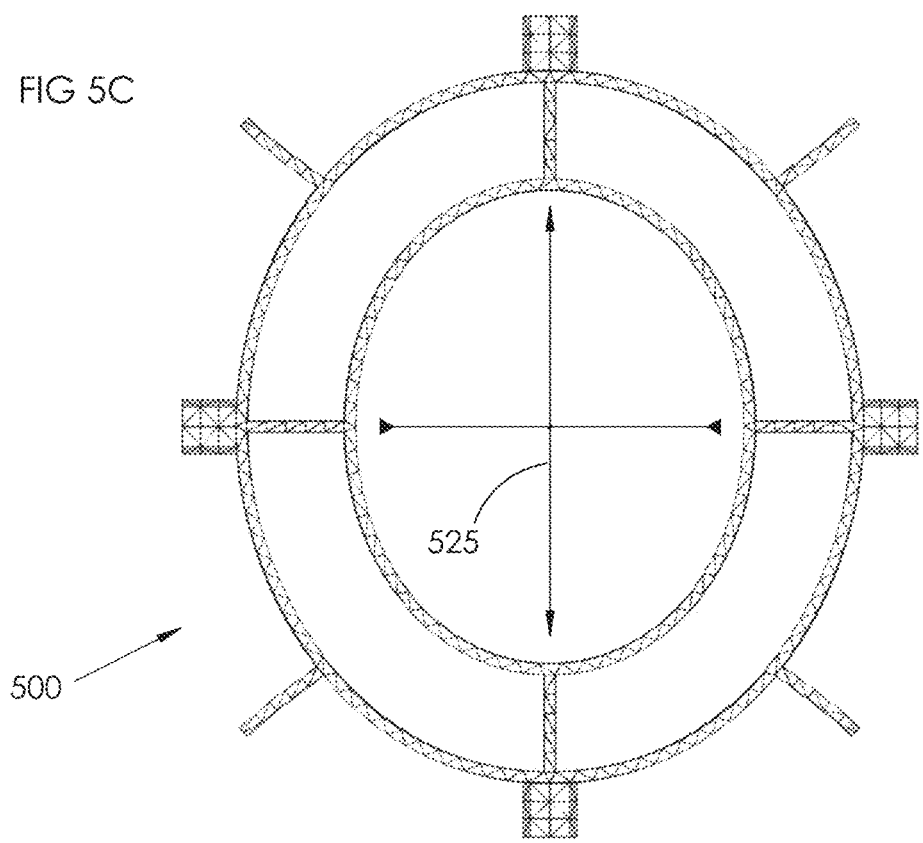
FIGS. 5C and 5D are two views of an example sensor element assembly shown as finite element analysis deflected shapes due to radial mode vibration.
Figure 5D:
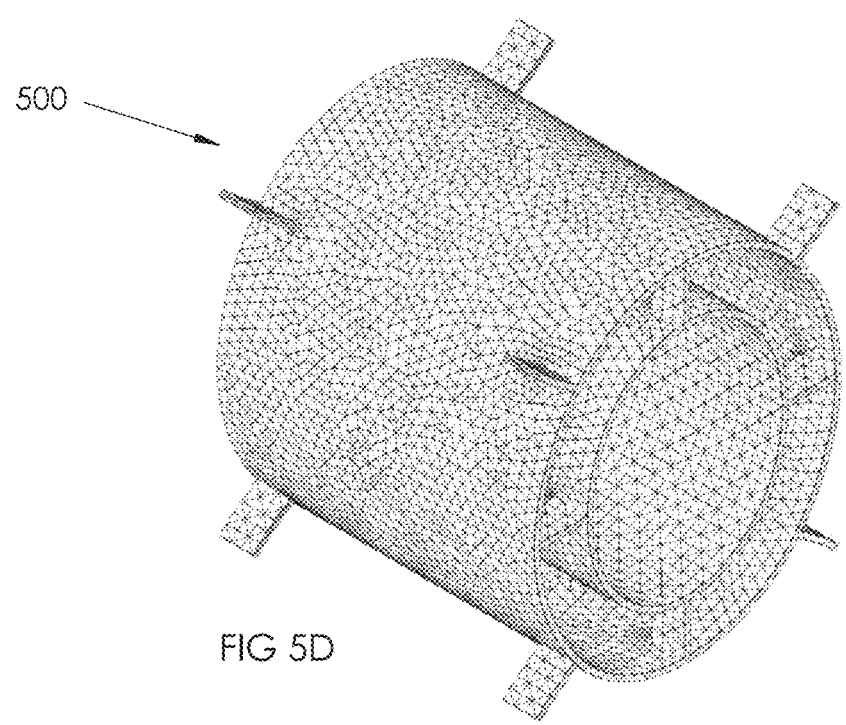

FIG. 5A is an isometric view of another example fluid parameter meter, where the sensor element assembly 500 has two sensor element conduits arranged in parallel as a concentric pair. FIG. 5B is a view down the central fluid flow axis of the example fluid parameter meter shown in FIG. 5A. FIGS. 5C and 5D are two views of an example sensor element assembly 500 shown as finite element analysis deflected shapes due to radial mode vibration.

In FIG. 5A, the fluid parameter meter has two concentric sensor elements 501 and 502 which are round straight metal conduits. Outer sensor element 501 has four mounting flexures 503 through 506 fixedly attached to the near (proximal) end and four mounting flexures 507 through 510 (507 not visible in this view) fixedly attached to the far (distal) end. Mounting flexures 503 through 510 may also be fixedly attached to the inside of an outer conduit 519. Magnets 521 through 524 are also fixedly attached to the outer sensor element 501 at its mid length position, and circumferentially rotated by 45 degrees from the mounting flexures 503 through 510 so that they coincide with vibration antinodes.

In an example, inner sensor element 502 is fixedly attached to mounting flexures 511 through 518 which are in circumferential alignment with magnets 521 through 524 so that they coincide with vibration antinodes of outer sensor element 501.

Sensor element assembly 500 can be substituted for sensor element assembly 200 as earlier described, and operated in the same way. An advantage of having two concentric sensor elements 501 and 502 connected by mounting flexures 511 through 518 is that both sensor elements 501 and 502 vibrate in unison 525 as shown in FIGS. 5C and 5D. This concentric arrangement minimizes velocity profile effects because more of the fluid is vibrated at the amplitude of the sensor elements, especially in the annular space between the sensor elements 501 and 502.

Figure 6A:
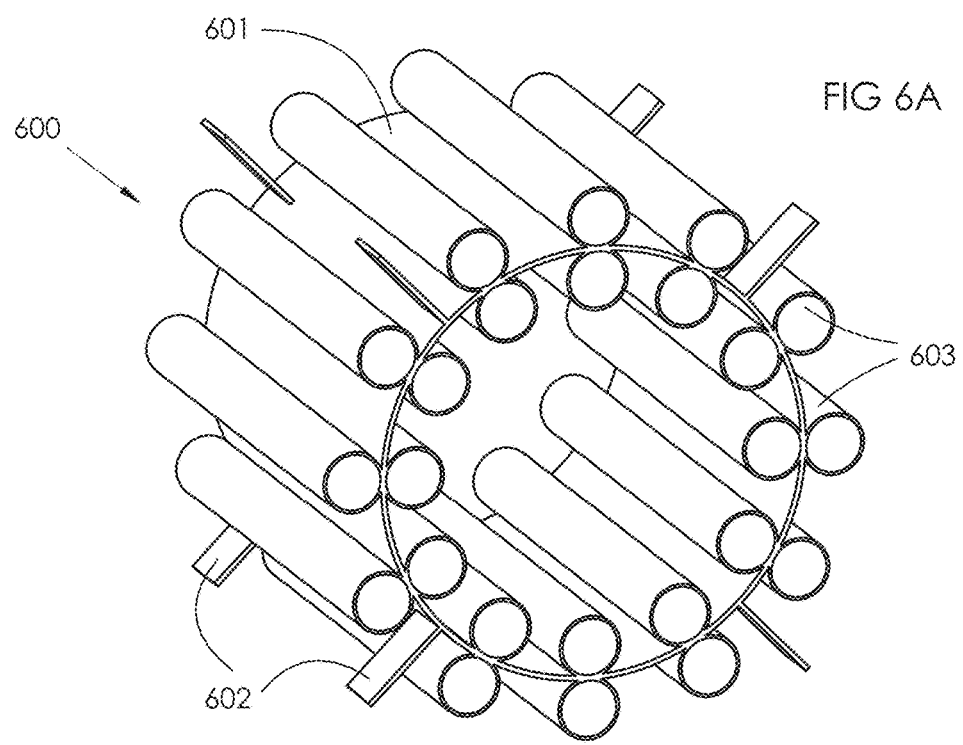
FIG. 6A is an isometric view of another example fluid parameter meter, where the sensor element assembly has of a plurality of sensor element conduits arranged in parallel clustered around a central sensor element.

FIG. 6A is an isometric view of another example fluid parameter meter, where the sensor element assembly 600 has of a plurality of sensor element conduits arranged in parallel clustered around a central sensor element. In FIG. 6A, a plurality of smaller sensor elements 603 are arranged around a central sensor element 601. As before, mounting flexures 602 may be fixedly attached to an outer conduit (not shown). No magnets are shown on this example for visual clarity but may be provided as described on earlier examples.

Figure 6B:
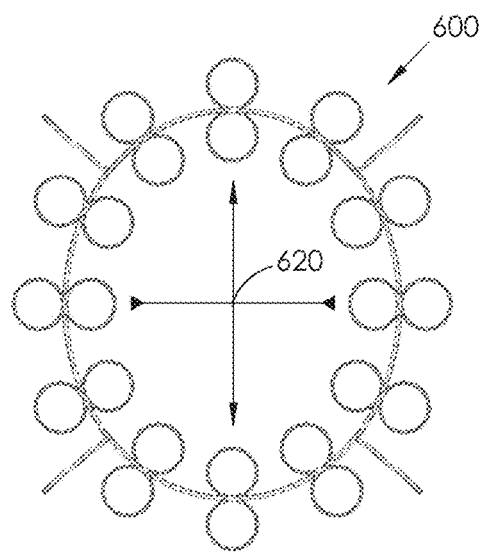
FIGS. 6B and 6C are two views of an example sensor element assembly shown as finite element analysis deflected shapes due to radial mode vibration.
Figure 6C:
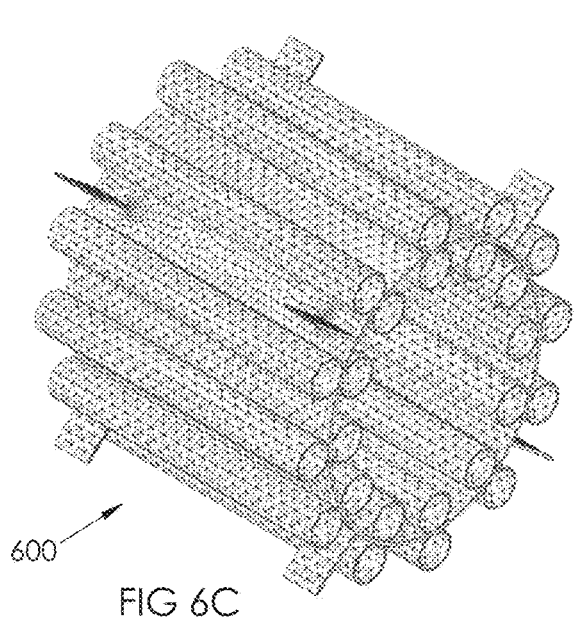

FIGS. 6B and 6C are two views of an example sensor element assembly 600 shown as finite element analysis deflected shapes due to radial mode vibration. An advantage to sensor element assembly 600 is that it reduces velocity profile effects because the smaller sensor elements 603 capture and vibrate the fluid at the same vibration amplitude 620 as the sensor element 601 thereby vibrating more of the fluid than may be vibrated by sensor element 601 alone.

In operation, sensor element assembly 600 may have 4 magnets attached at the mid length position (not shown) at the antinodes of vibration 620, and may be operated as earlier described for sensor element assembly 200.

Figure 7A:
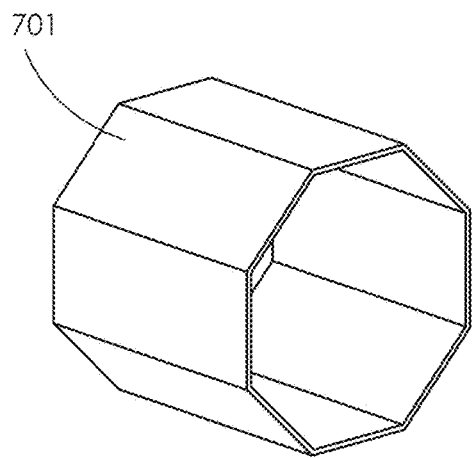
FIG. 7A through 7D show example sensor element shapes that are non-circular.
Figure 7B:
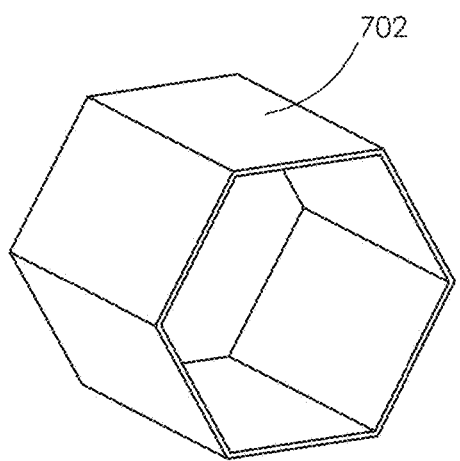
Figure 7C:
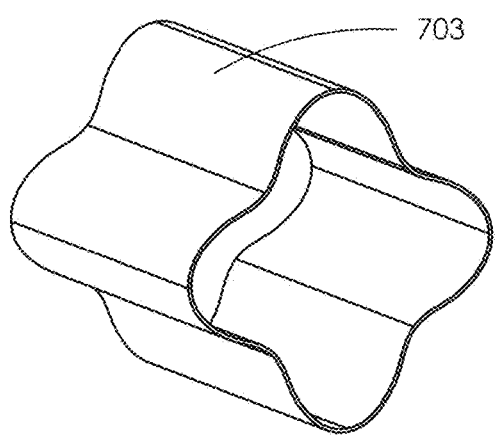
Figure 7D:
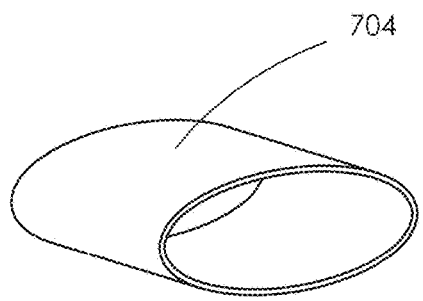

FIG. 7A through 7D show example sensor element shapes that are non-circular. FIG. 7A shows an example of an octagonal sensor element 701. FIG. 7B shows an example of a hexagonal sensor element 702. FIG. 7C shows an example of a four-lobed clover leaf shaped sensor element 703. FIG. 7D shows an example of an oval or elliptical shaped sensor element 704. Any of the shapes of sensor elements 701 through 704 and others can be used.

Figure 8:
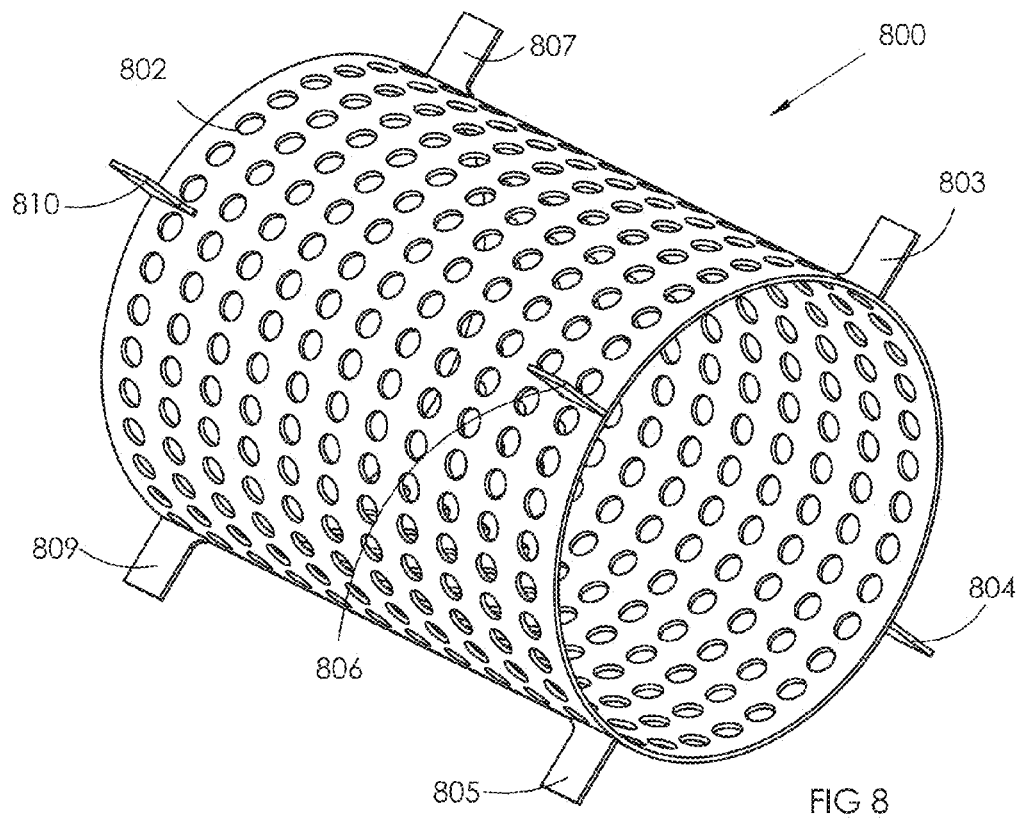
FIG. 8 is an isometric view of another example sensor element assembly having a pattern of openings or holes in sensor element.

FIG. 8 is an isometric view of another example sensor element assembly 800 having a pattern of openings or holes in sensor element. In this example, the sensor element assembly 800 includes sensor element 801, which is a round straight section of metal conduit. Sensor element 801 includes hole pattern 802 allowing fluid to flow between the inside and the outside of sensor element 801. Sensor element 801 also includes mounting flexures 803 through 810 which are metal fins of the same approximate thickness as is sensor element 801 and are arranged in the same manner and fixedly attached in the same manner as earlier described for sensor element assembly 200. No magnets are shown for visual clarity, but may be provided as in earlier examples.

An advantage of having hole pattern 802 in sensor element 801 is that it allows fluid flow between the inside and the outside of sensor element 801 and thereby reduces wall effects. As the annular space between a sensor element and an outer conduit becomes smaller, fluid becomes more trapped there between. This entrapment of fluid inhibits the fluid's ability to move and accelerate under the influence of a vibrating sensor element. This inhibiting effect changes the vibrational frequency and damping characteristics of the sensor element assembly, and also changes the meters sensitivity to measuring fluid density and viscosity. Making the annular space large is sometimes not practical due to space constraints in a particular configuration, therefore by adding hole pattern 802, the vibration inhibiting affect is minimized or eliminated.

Figure 9A:
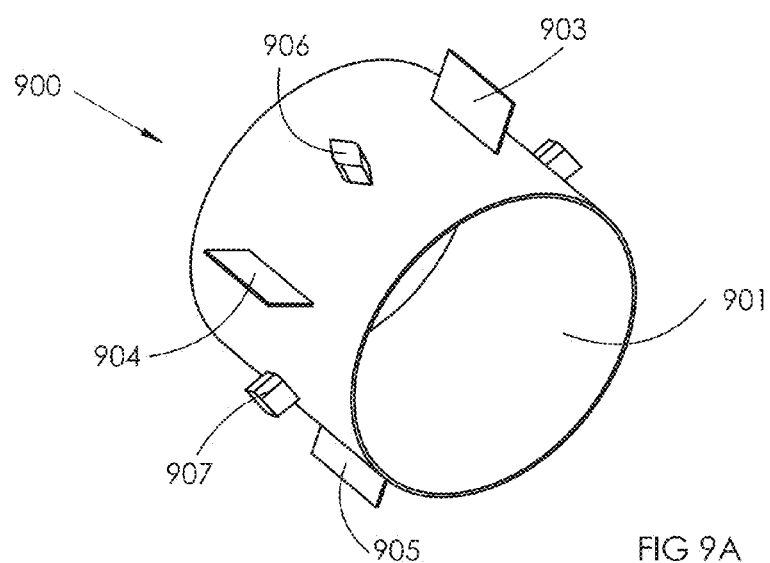
FIG. 9A is an isometric view of an example sensor element assembly having four mounting flexures arranged at the mid length position of the sensor element, and having hydro-dynamically shaped magnet guards to protect the magnets.

FIG. 9A is an isometric view of an example sensor element assembly 900 having four mounting flexures arranged at the mid length position of the sensor element, and having hydro-dynamically shaped magnet guards to protect the magnets. Sensor element assembly 900 is shown including sensor element 901, which is a round straight tubular sensor element made of metal and includes four mounting flexures 902 through 905 (902 not visible in this view). Mounting flexures 902 through 905 are located at the mid length position of sensor element 901 and are mounted along its node areas where vibration amplitude is minimal. Magnet assemblies 906 through 909 (908 is not visible in this view) are configured having hydro-dynamically shaped magnet guards to protect them from abrasion. Magnet assemblies 906 through 909 are circumferentially rotated 45 degrees from the mounting flexures 902 through 905 so that they are located in anti-node areas of maximum deflection. In operation, sensor element assembly may be operated in the same way as was earlier described for sensor element assembly 200.

Figure 9B:
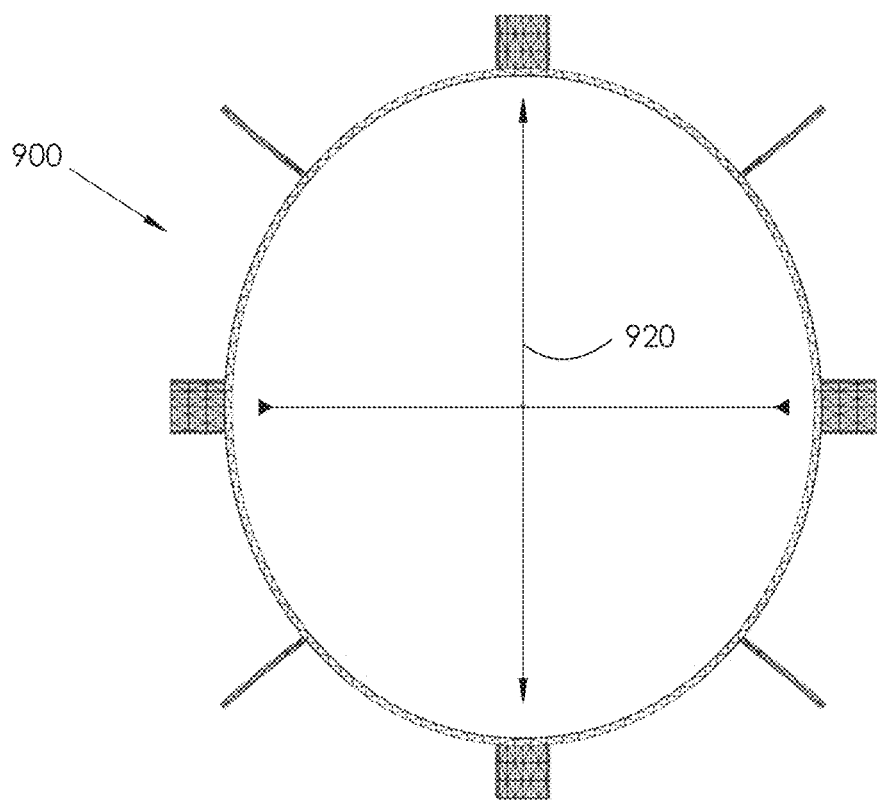
FIGS. 9B and 9C are two views of an example sensor element assembly shown as finite element analysis deflected shapes due to radial mode vibration.
Figure 9C:
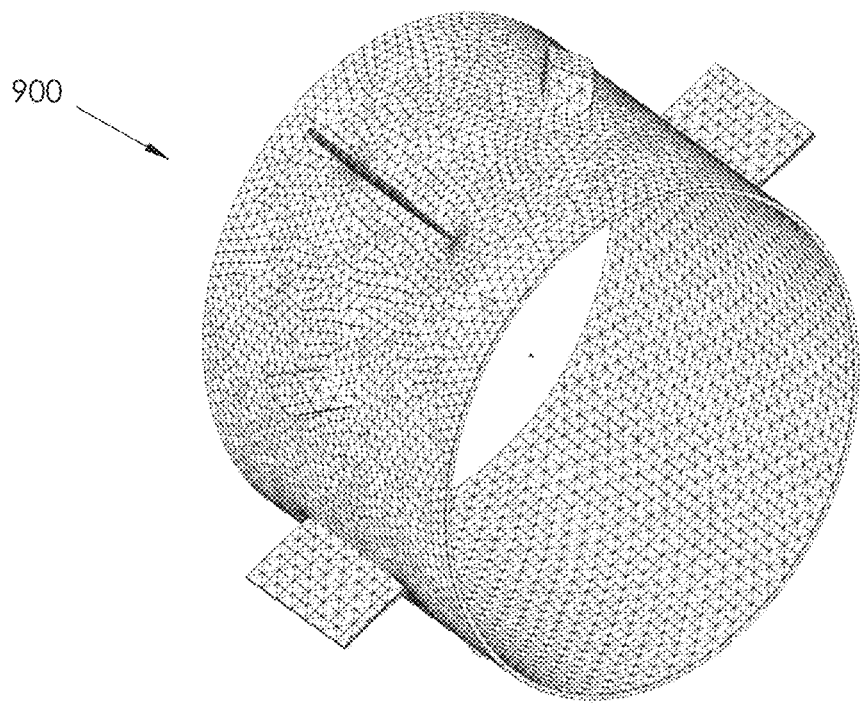

FIGS. 9B and 9C are two views of an example sensor element 900 assembly shown as finite element analysis deflected shapes due to radial mode vibration. FIGS. 9B and 9C show a finite element analysis plot of how the vibration shape 920 of sensor element assembly 900 is elliptical and uniform along its length.

Figure 10:
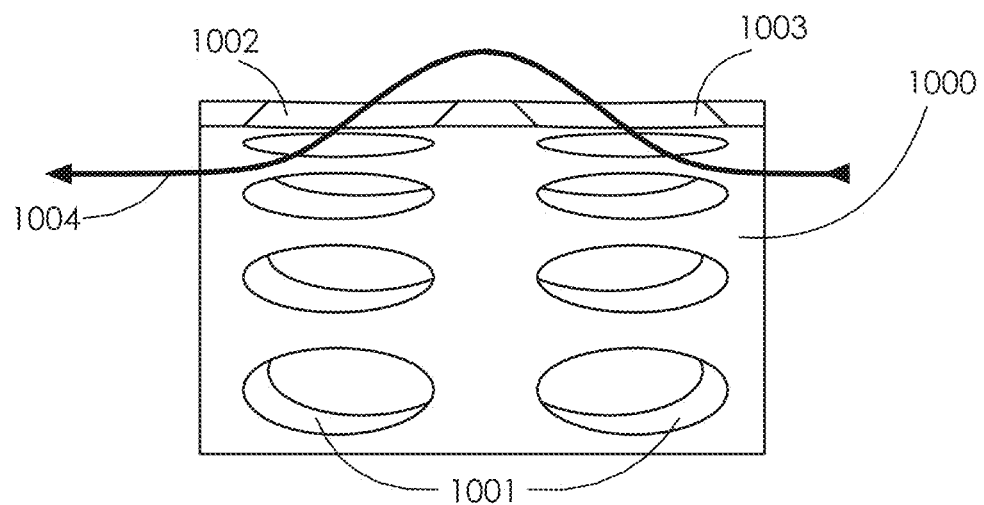

FIG. 10 is a close up cross section view of an example sensor element 1000 having a pattern where the openings are specifically shaped to induce fluid flow there through. Sensor element 1000 includes hole pattern 1001 where the holes are specifically shaped in such a way to induce fluid flow 1004 to pass through from the outside in through hole 1002 and from the inside out through hole 1003 as shown in FIG. 10. This example configuration can decrease wall effects and particle slippage and velocity profile effects, especially in low viscosity fluids because it induces more particle-tube interaction. The shape of the holes in hole pattern 1001 can be angled as shown in FIG. 10 by laser cutting, or punching, or machining, or other forming methods.

Figure 11:
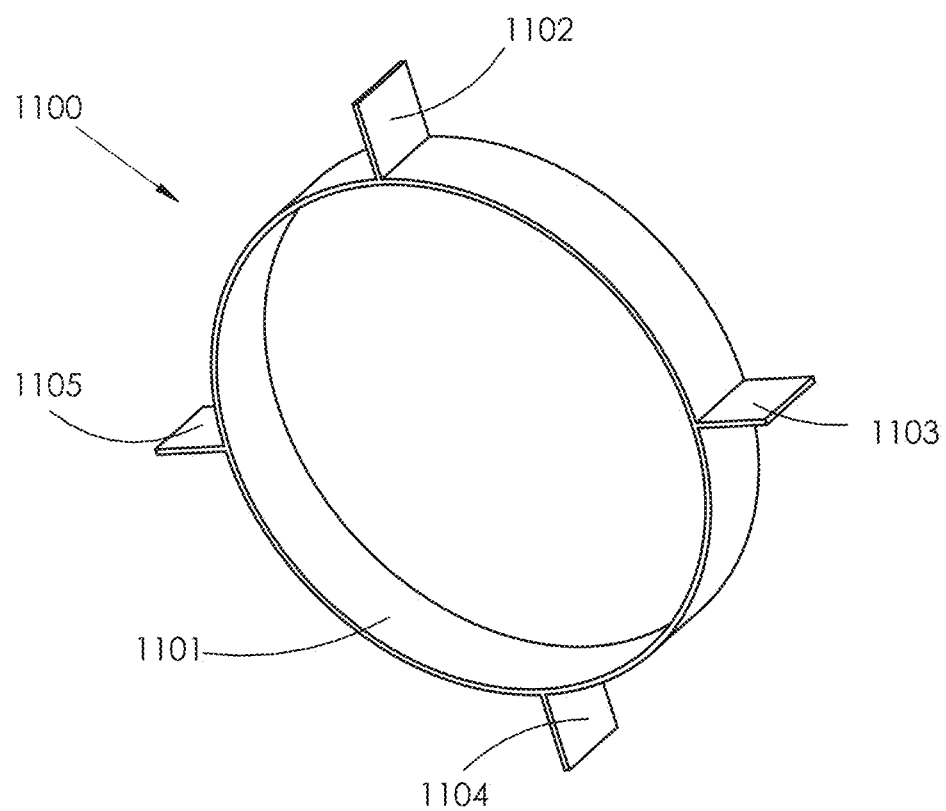
FIG. 11 is an example wear guard configured to protect the leading edges of a sensor element assembly from abrasive wear.

FIG. 11 is an example wear guard 1100 configured to protect the leading edges of a sensor element assembly from abrasive wear. Abrasive wear was earlier described as most severe on the leading edges of the sensor element and on the mounting flexures. Therefore, an example wear guard 1100 is shown having the same cross sectional shape perpendicular to the direction of fluid flow as does the sensor element assembly it is to guard. Wear guard 1100 is therefore comprised of guard element 1101, and guard mounting supports 1102 through 1105 all of which have a similar size and shape as a sensor element assembly it is configured to guard. When mounted upstream from a sensor element assembly, the wear guard 1100 takes the brunt of the direct impingement of the abrasive wear and protects the leading edges of any sensor element assembly located downstream.

Figure 12:
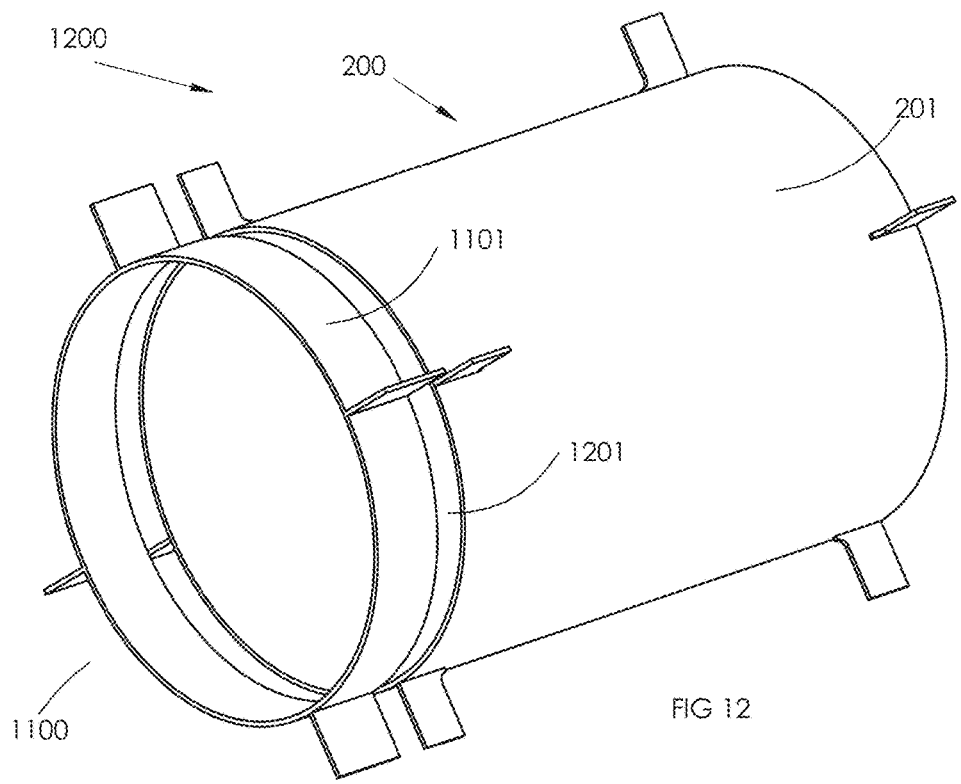
FIG. 12 is an oblique view of an example sensor element assembly and wear guard shown in alignment for protecting the sensor element assembly from abrasive wear.

FIG. 12 is an oblique view of an example sensor element assembly and wear guard 1100 shown in alignment for protecting the sensor element assembly from abrasive wear. FIG. 12 shows the just described assembly of wear guard 1100 and sensor element assembly 200. Sensor element 201 is coaxially aligned with guard element 1101 and spaced apart to leave a gap 1201 there between. By using wear guard 1100 upstream from sensor element assembly 200, direct impingement of abrasive particles on the leading edges of sensor element assembly 200 is avoided, and wear is therefore minimized.

FIG. 13 is a graph illustrating a relationship between vibration period squared versus fluid specific gravity for an example fluid parameter meter, to determine fluid density from vibration period. The values given in Table 1 described previously are plotted along curve 1300 showing the generally linear relationship between vibration period squared, and fluid specific gravity SG as was earlier described.

FIG. 14 is a block diagram showing signal processing for an example fluid parameter meter. The function of signal processing block diagram 1400 was earlier described with reference to fluid parameter meter 100. Signal processing diagram 1400 is representative of many of the sensor embodiments previously described and can be used with any of them with some variations for having more driving and sensing transducers for some of the examples shown.

Figure 15A:
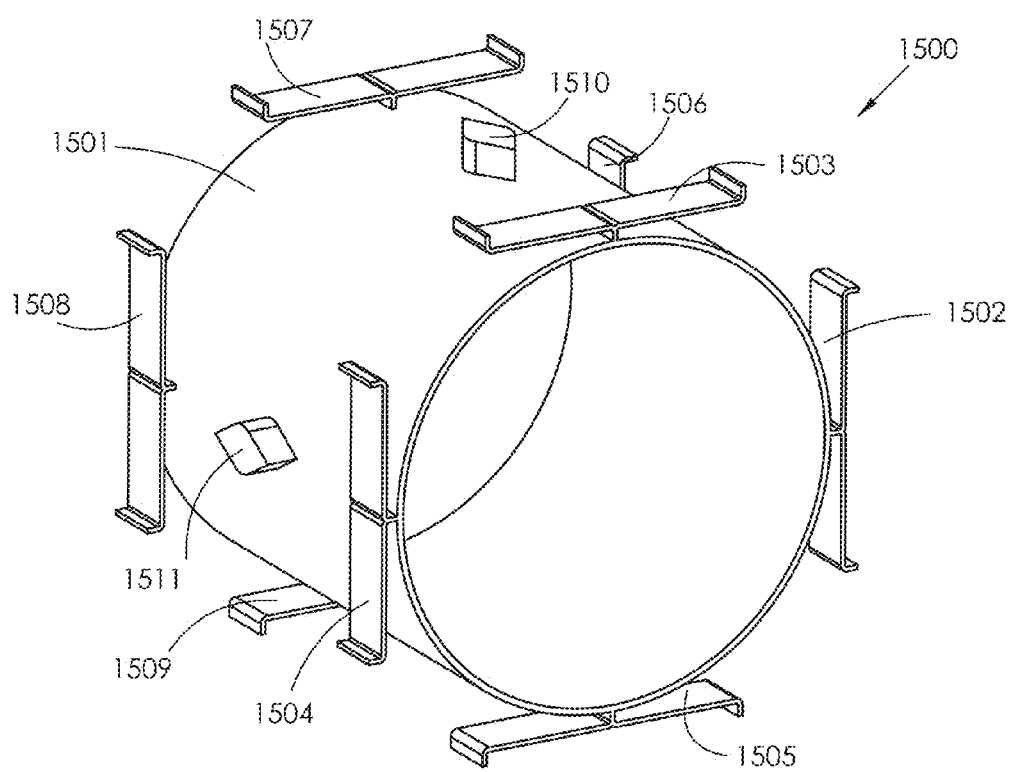
FIG. 15A is an isometric view of an example sensor element assembly, where the mounting flexures are arranged tangent to the sensor element and are attached to the sensor element on anti-nodal areas.

FIG. 15A is an isometric view of an example sensor element assembly 1500, where the mounting flexures are arranged tangent to the sensor element and are attached to the sensor element on anti-nodal areas. Example sensor element assembly 1500 includes sensor element 1501, and mounting flexures 1502 through 1509 (1509 is not visible in this view) are mounted generally tangent to the surface of sensor element 1501 on the anti-node areas; rather than being mounted radially in node areas as was the case for the previous examples. Mounting flexures 1502 through 1509 have a thickness perpendicular to the direction of fluid flow similar to sensor element 1501 to minimize obstruction to flow. Mounting flexures 1502 through 1509 also include bends to facilitate mounting and to facilitate a specified stiffness.

An advantage of arranging the mounting flexures 1502 through 1509 tangentially as shown, is that the natural modes of vibration can be less influenced by the stiffness of the mounting flexures, and the stress in the mounting flexures 1502 through 1509 can be configured to have lower values because they can be made to be any length regardless of the width of the annular space between the sensor element 1501 and the outer conduit in which it may be mounted (not shown). Magnets 1510 through 1513 (magnets 1512 and 1513 not visible in this view) are hydro-dynamically shaped to prevent abrasive wear.

Figure 15B:
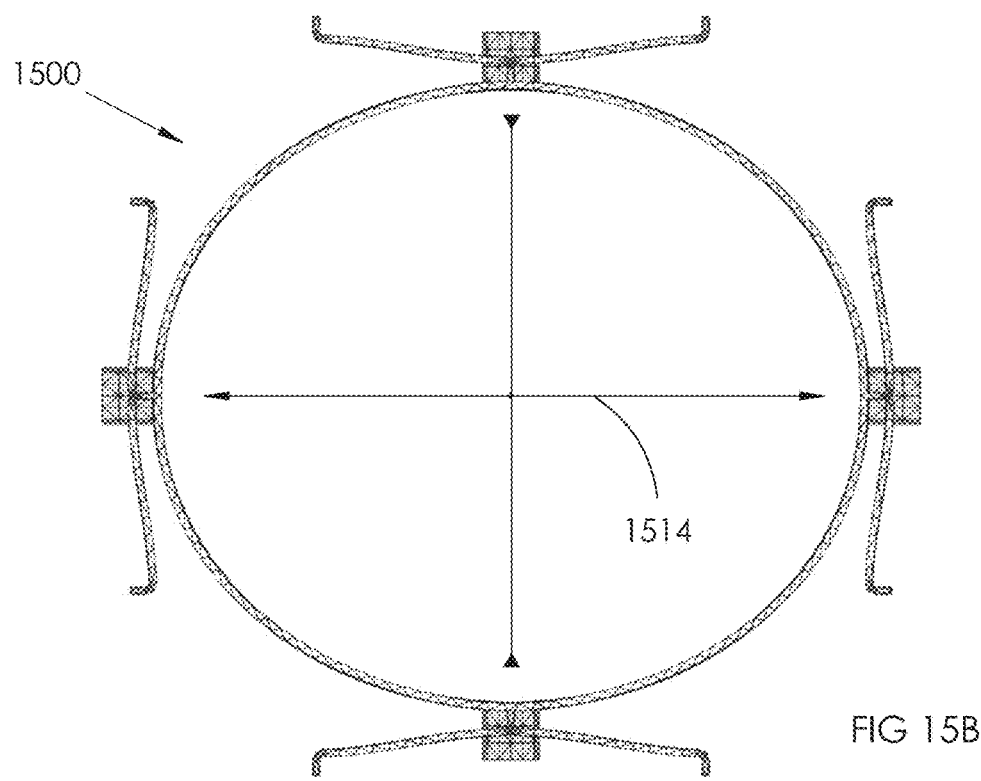
FIGS. 15B and 15C are two views of the example sensor element assembly of FIG. 15A shown as Finite Element deflected shapes from a selected mode of vibration.
Figure 15C:
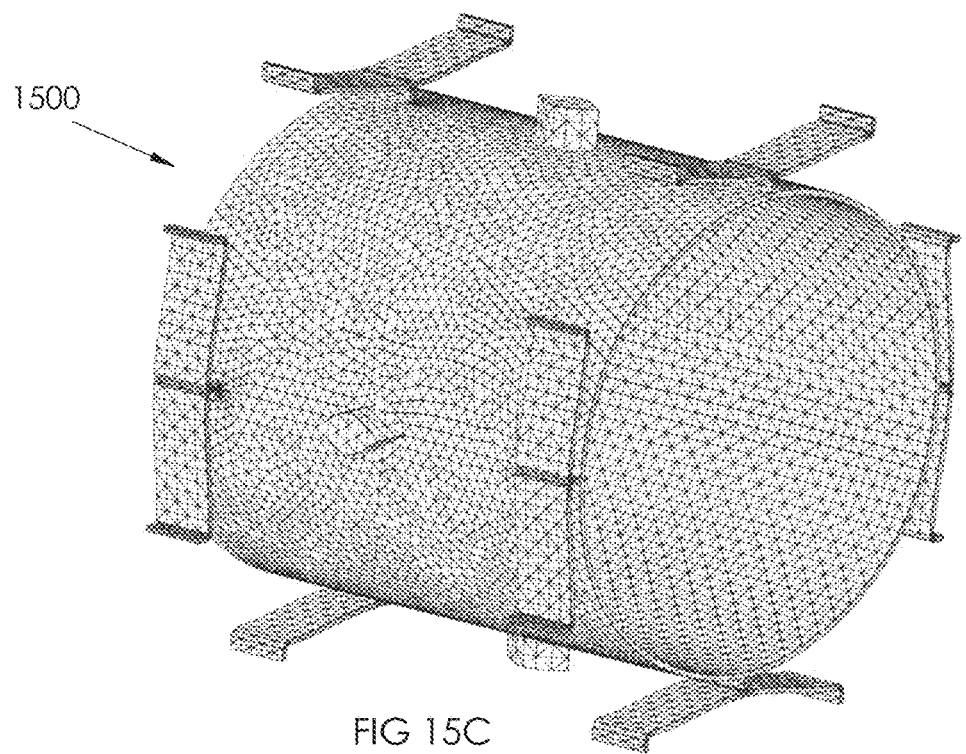

FIGS. 15B and 15C are two views of the example sensor element assembly of FIG. 15A shown as Finite Element deflected shapes from a selected mode of vibration. FIGS. 15B and 15C are finite element analysis deflected shape predictions for an example mode of vibration of sensor element assembly 1500 and show the vibration deflected shape 1514. Sensor element assembly 1500 can be provided as a direct replacement for sensor element assembly 200 and functions in the same way as previously described.

Figure 16A:
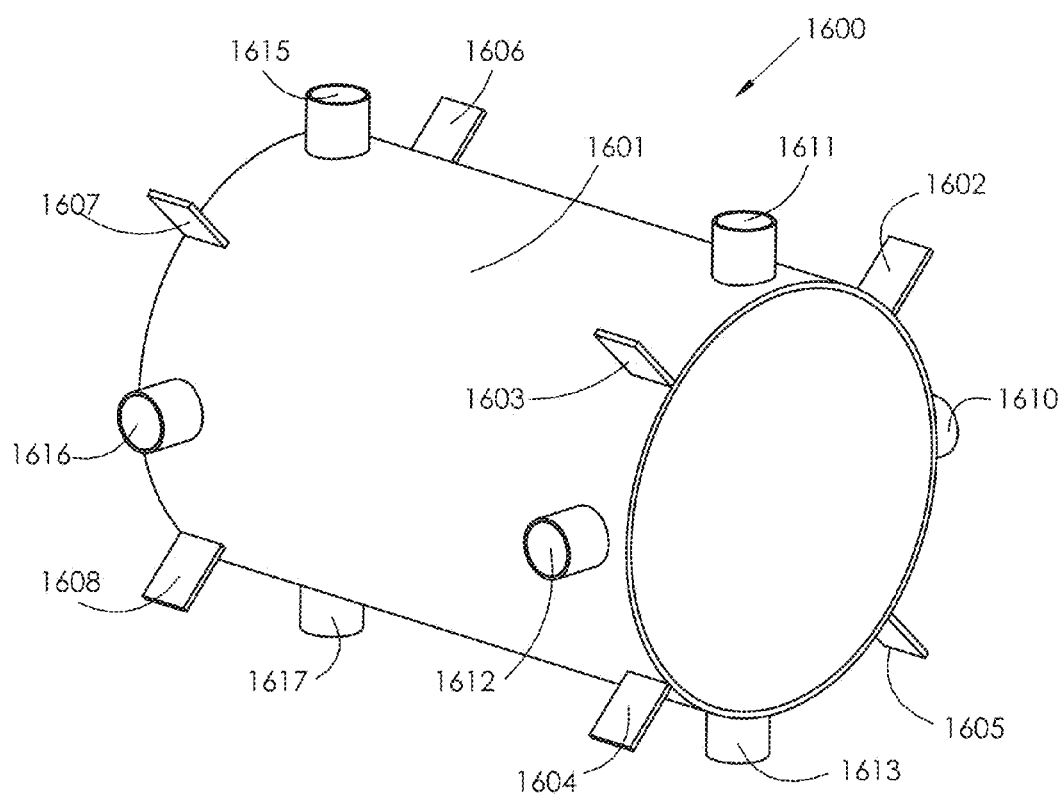
FIG. 16A is an isometric view of another example fluid parameter meter, where the sensor element assembly has sets of transducer magnets arranged near both ends of sensor element to facilitate multiple modes of vibration and mode shapes that invert along the length of the sensor element.
Figure 16B:
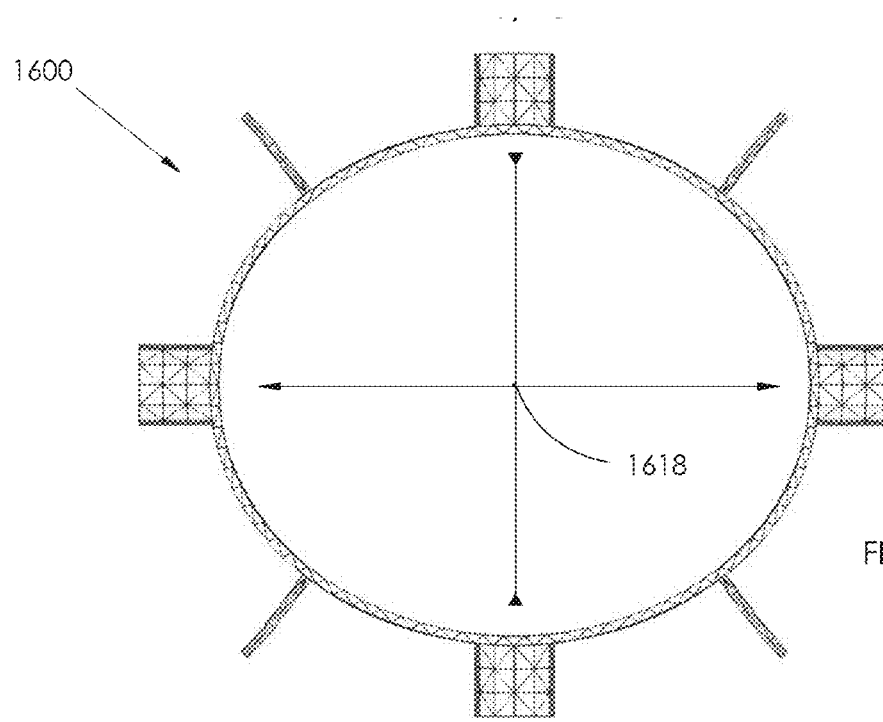
FIGS. 16B and 16C are two views of the example sensor element assembly shown as Finite Element Analysis deflected shapes from a selected mode of vibration.
Figure 16C:
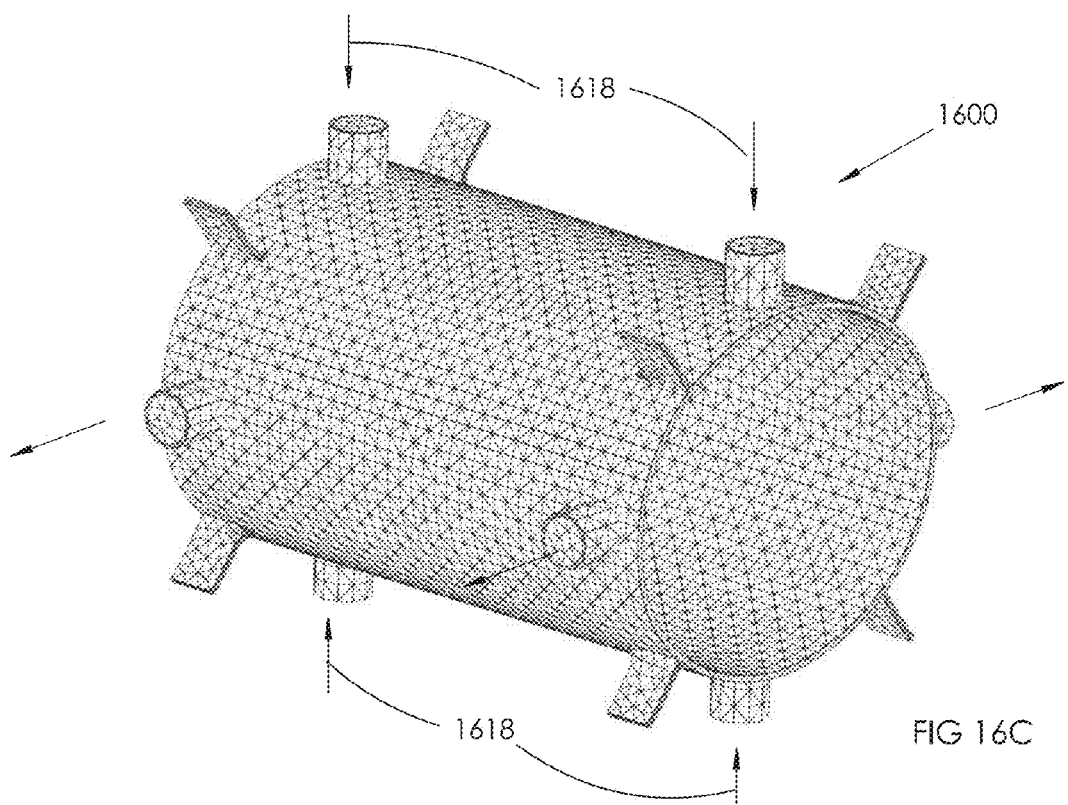
Figure 16D:
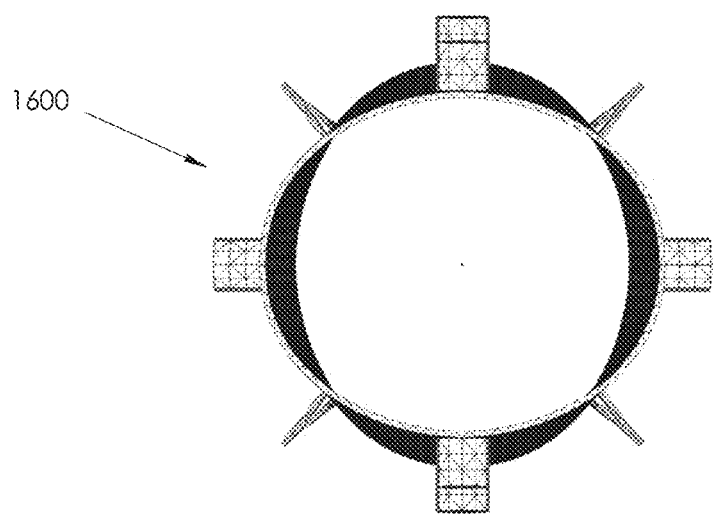
FIGS. 16D and 16E are two views of the example sensor element assembly shown as Finite Element Analysis deflected shapes from a selected mode of vibration, where the radial mode shape inverts along the length of the sensor element.
Figure 16E:
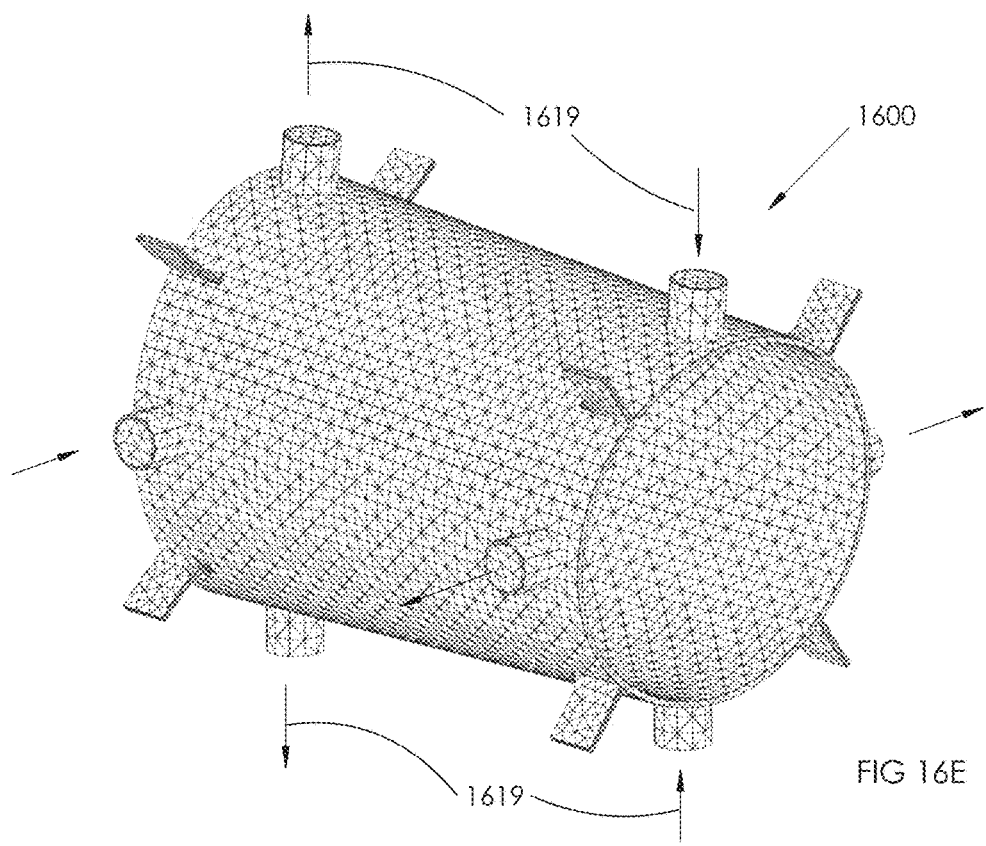

FIG. 16A is an isometric view of another example fluid parameter meter, where the sensor element assembly has sets of transducer magnets arranged near both ends of sensor element to facilitate multiple modes of vibration and mode shapes that invert along the length of the sensor element. FIGS. 16B and 16C are two views of the example sensor element assembly shown as Finite Element Analysis deflected shapes from a selected mode of vibration. FIGS. 16D and 16E are two views of the example sensor element assembly shown as Finite Element Analysis deflected shapes from a selected mode of vibration, where the radial mode shape inverts along the length of the sensor element.

FIG. 16A shows another example where a set of four magnets 1610 through 1613 are arranged near the lower right proximal end of sensor element 1601, and another set of four magnets 1614 through 1617 are arranged near the upper left distal end of sensor element 1601. This arrangement allows for modes of vibration that invert in shape along the length of sensor element 1601, as well as modes that do not invert along the length of sensor element 1601. Each magnet 1610 through 1617 is accompanied by a corresponding coil not shown (for visual clarity) in FIG. 16A through 16E (but shown in FIG. 17 as having the same magnet number and an "A" designation thereafter). Coils 1610A and 1612A are wired together to act as one coil to sense radial mode shape vibration at the proximal end of sensor element 1601. Coils 1614A and 1616A are wired together to act as one coil to sense radial mode shape vibration at the distal end of sensor element 1601.

FIGS. 16B and 16C are finite element deflected shape predictions of sensor element assembly 1600 where the selected mode shape motion 1618 is elliptical in cross section shape and is uniform along the length of sensor element 1601. FIGS. 16D and 16E are finite element deflected shape predictions of sensor element assembly 1600 where the selected mode shape motion 1619 is elliptical in cross section shape and is not uniform along the length of sensor element 1601, but instead the deflection shape 1619 inverts once from the distal end to the proximal end of sensor element 1601. This mode shape can causes Coriolis forces along the length of sensor element 1601 which in turn cause Coriolis deflections similar to deflected shape 1618. This feature measures fluid flow rate using the Coriolis effect as next described.

Figure 17:
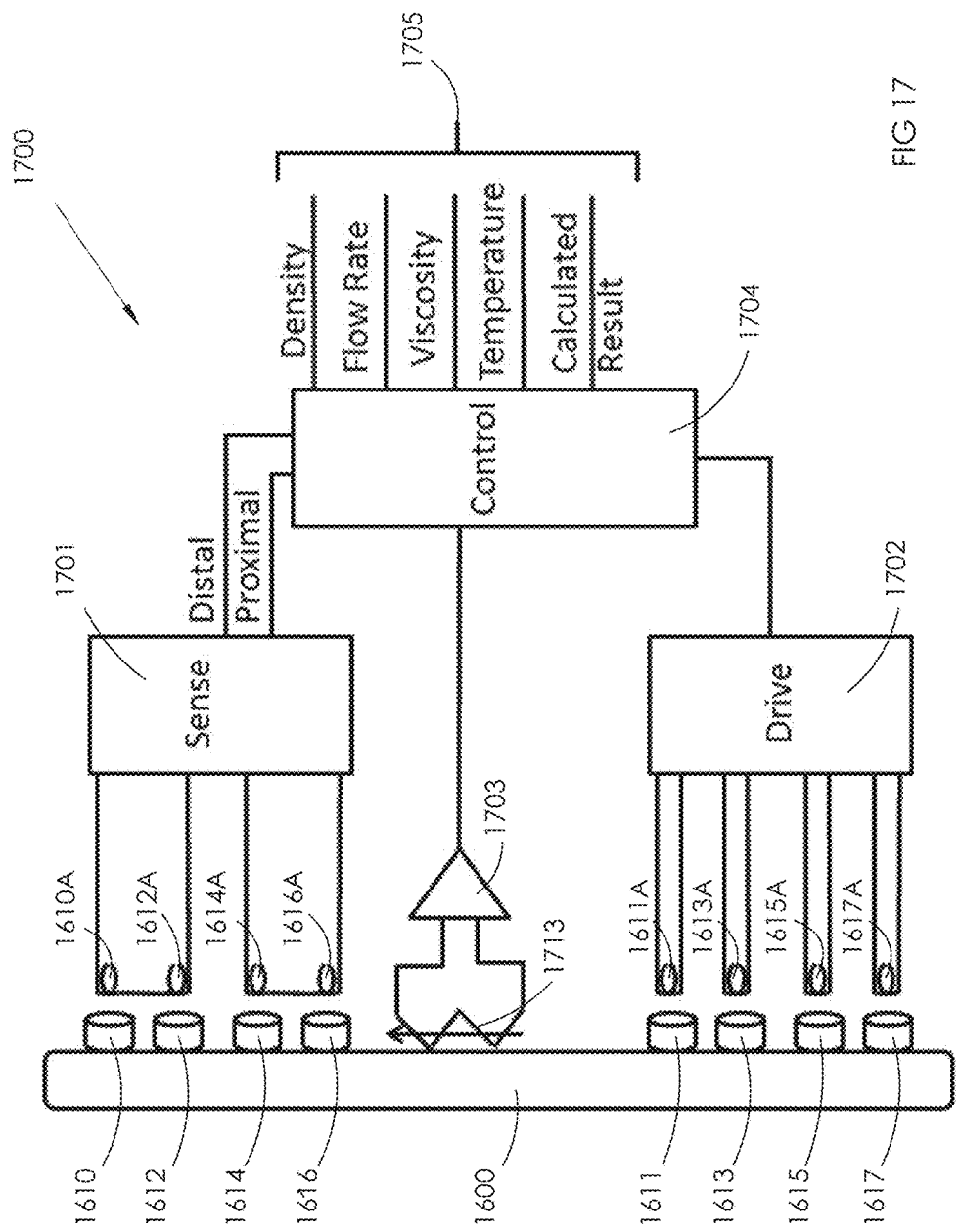
FIG. 17 is a block diagram showing signal processing for an example fluid parameter meter, where fluid flow rate is determined along with other fluid parameters.

FIG. 17 is a block diagram showing signal processing for an example fluid parameter meter, where fluid flow rate is determined along with other fluid parameters. Temperature sensor 1713 is shown in FIG. 17 but not in FIG. 16A through 16E for visual clarity. Temperature sensor 1713 along with amplifier 1703 measures the temperature of the fluid flowing in and around sensor element assembly 1600 and relays that signal to control module 1704 for thermal affect compensation and for reporting as a temperature output signal 1705.

The circuit shown in FIG. 17 may be provided in conjunction with sensor element assembly 1600. To cause Coriolis forces along the sensor element 1601, vibration shape 1619 is induced to vibrate by amplifier 1702 driving magnet coil pairs 1611(A) and 1613(A) together in phase with each other, but out of phase by 180° from driving magnet coil pairs 1615(A) and 1617(A).

In an example, to sense the driven vibration of motion shape 1619, signals from magnet coil pairs 1610(A) and 1612(A) are sensed by amplifier 1701 representing the radial motion at the proximal end of sensor element 1601. Similarly, signals from magnet coil pairs 1614(A) and 1616(A) are sensed by amplifier 1701 representing the radial motion at the distal end of sensor element 1601. These signals are received by control module 1704 to provide both drive control signals back to driving amplifier 1702 for drive control, and to determine fluid parameters such as fluid density, viscosity, temperature, flow rate, and other calculated results such as PPA, GVF, Net-oil, and others.

In an example, to determine fluid flow rate, Control module 1704 calculates the phase or time difference between the distal end motion and the proximal end motion of sensor element 1601. This phase difference can be proportionally related to the flow rate of fluid passing through sensor element assembly 1600.

In an example, to determine the fluid parameters of density, viscosity, temperature, and other calculated results, the same methods may be applied that were previously discussed for the example of FIG. 1. In another example, the calculated result of Reynolds Number may be determined as being a function of the measured parameters of flow rate velocity, density and viscosity, and the pipe diameter, which are all known or measured by the meter. In another example the calculated result of kinematic viscosity can be calculated from the absolute, sometimes called the (dynamic) viscosity and the fluid density which is measured by the meter.

Figure 18A:
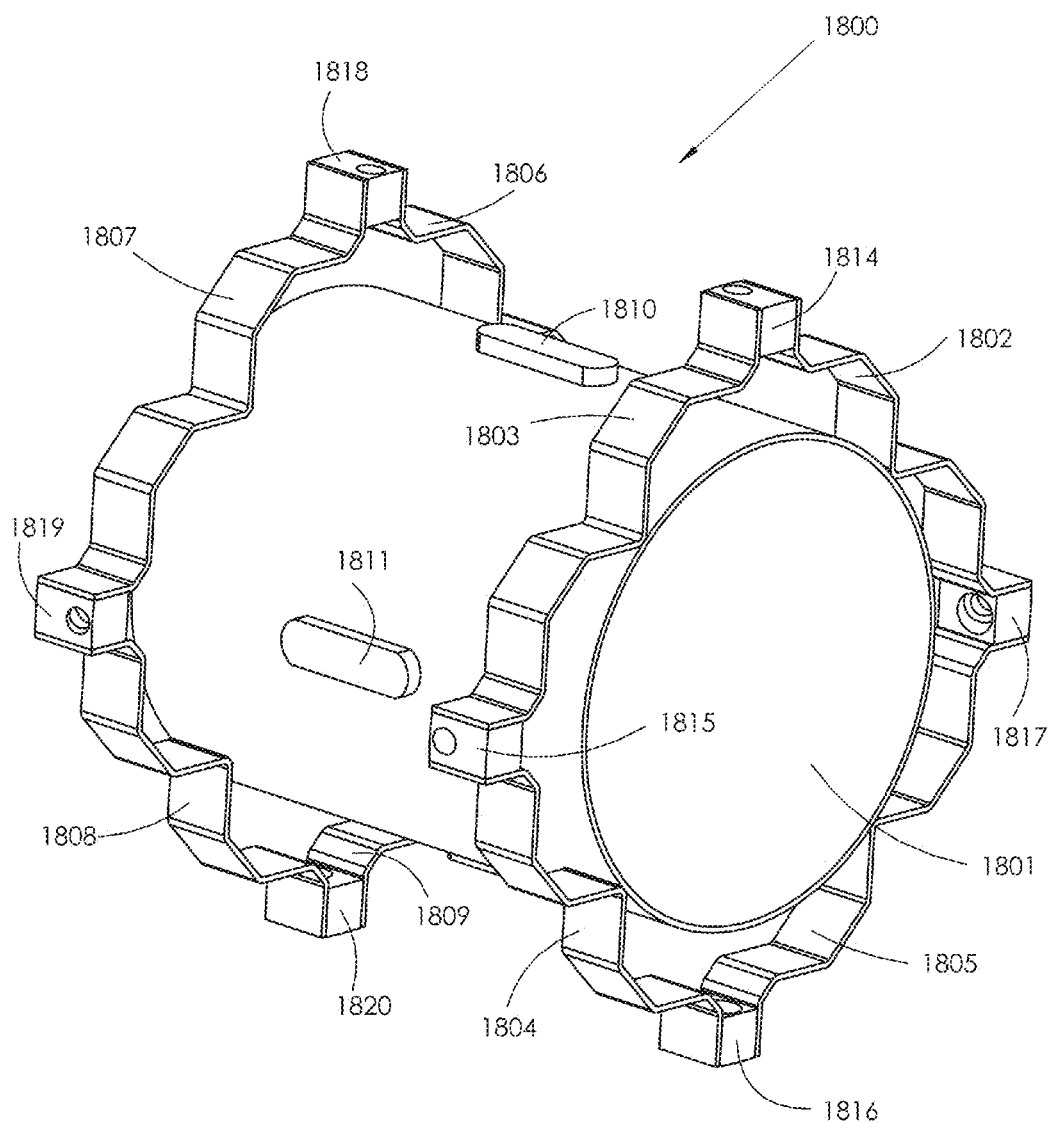
FIG. 18A is an isometric view of an example sensor element assembly, where the mounting flexures are arranged tangent to the sensor element and are attached to the sensor element on nodal areas.
Figure 18B:
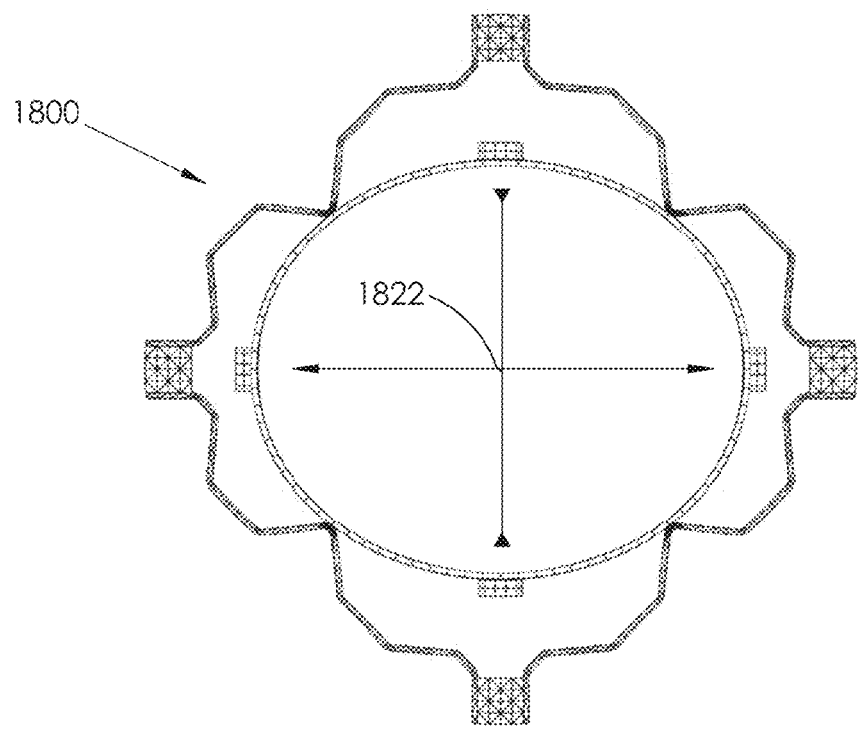
FIGS. 18B and 18C are two views of the example sensor element assembly of FIG. 18A, shown as Finite Element deflected shapes from a selected mode of vibration.
Figure 18C:
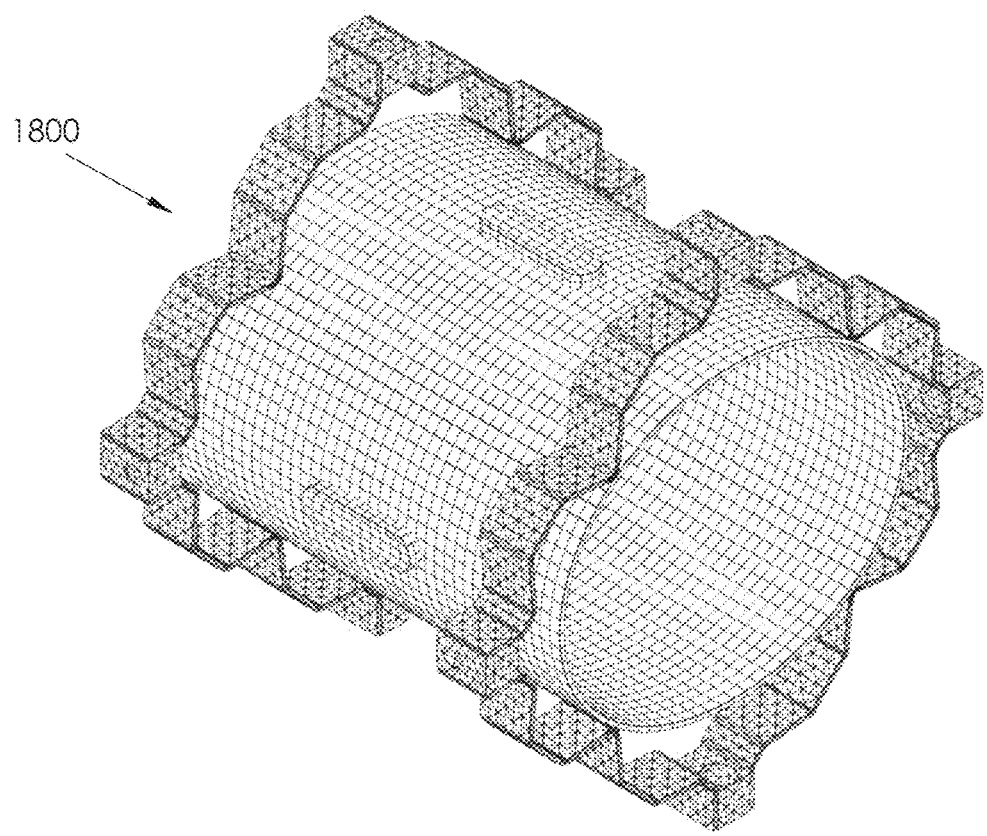

FIG. 18A is an isometric view of an example sensor element assembly 1800, where the mounting flexures are arranged tangent to the sensor element and are attached to the sensor element on nodal areas. FIGS. 18B and 18C are two views of the example sensor element assembly of FIG. 18A, shown as Finite Element deflected shapes from a selected mode of vibration.

The example sensor element assembly 1800 includes sensor element 1801, and mounting flexures 1802 through 1809 are mounted generally tangent to the surface of sensor element 1801 along their mid-spans, and on the nodal areas of sensor element 1801 for selected modes of vibration. Mounting flexures 1802 through 1809 have a thickness perpendicular to the direction of fluid flow similar to sensor element 1801 to minimize obstruction to flow. Mounting flexures 1802 through 1809 can include bends to facilitate mounting and to facilitate a specified stiffness. Mounting flexures 1802 through 1809 are fixedly attached to mounting blocks 1814 through 1821 (mounting block 1821 not visible in this view) at their distal ends.

In an example, mounting blocks 1814 through 1824 are configured to allow mounting the entire sensor assembly 1800 to the outer conduit (not shown in this view). Mounting blocks 1814 through 1824 can be fixedly attached to an outer conduit by any means including brazing, welding, adhesion, or by bolting through holes as is shown in this example.

An advantage of arranging the mounting flexures 1802 through 1809 as shown, is that the natural modes of vibration can be less influenced by the properties of the mounting flexures, and the stress in the mounting flexures 1802 through 1809 can be configured to have specific or lower values because they can be made to be any stiffness regardless of the width of the annular space between the sensor element 1801 and the outer conduit in which it may be mounted (not shown).

Instead of the magnets in previous examples for driving and sensing the vibration of sensor assembly 1801, in this example, armatures 1810 through 1813 (armatures 1812 and 1813 not visible in this view) magnetically couple sensor assembly 1801 to driving and sensing electro-magnetic coils (not shown in this view) outside of an outer conduit.

Armatures 1810 through 1813 may be made of magnetically permeable material such as carbon steel, type 410 stainless steel, type 430 stainless steel, Carpenter Steel Corporation High Permeability Alloy 49, HyMu 80 alloy, transformer iron, silicon iron, ferrite, and the like. Armatures 1810 through 1813 may be fixedly attached to sensor element 1801 by any method including brazing, welding, adhesion, fusion bonding, and the like.

If the material of sensor element 1801 is magnetically permeable, then armatures 1810 through 1813 may not be provided because the wall of sensor element 1801 can function as an armature thereby magnetically coupling with driving and sensing coils outside of an outer conduit (not shown).

FIGS. 18B and 18C are finite element analysis deflected shape predictions for an example mode of vibration of sensor element assembly 1800 and show the vibration deflected shape motion 1822. Sensor element assembly 1800 may be a direct replacement for sensor element assembly 200 and may function in the same way as previously described.

Additional Micro Electro Mechanical Sensors, MEMS, may be incorporated into the meter that provide complementary fluid process variable measurements, which may be used either individually and/or in combination with existing meter process fluid measurements. Resulting in either all new process meter fluid outputs and/or compensations that may improve existing meter process fluid outputs. These MEMS transducers may include but are not limited to pressure, pH, ultrasonic, acceleration, etc.

Figure 19A:
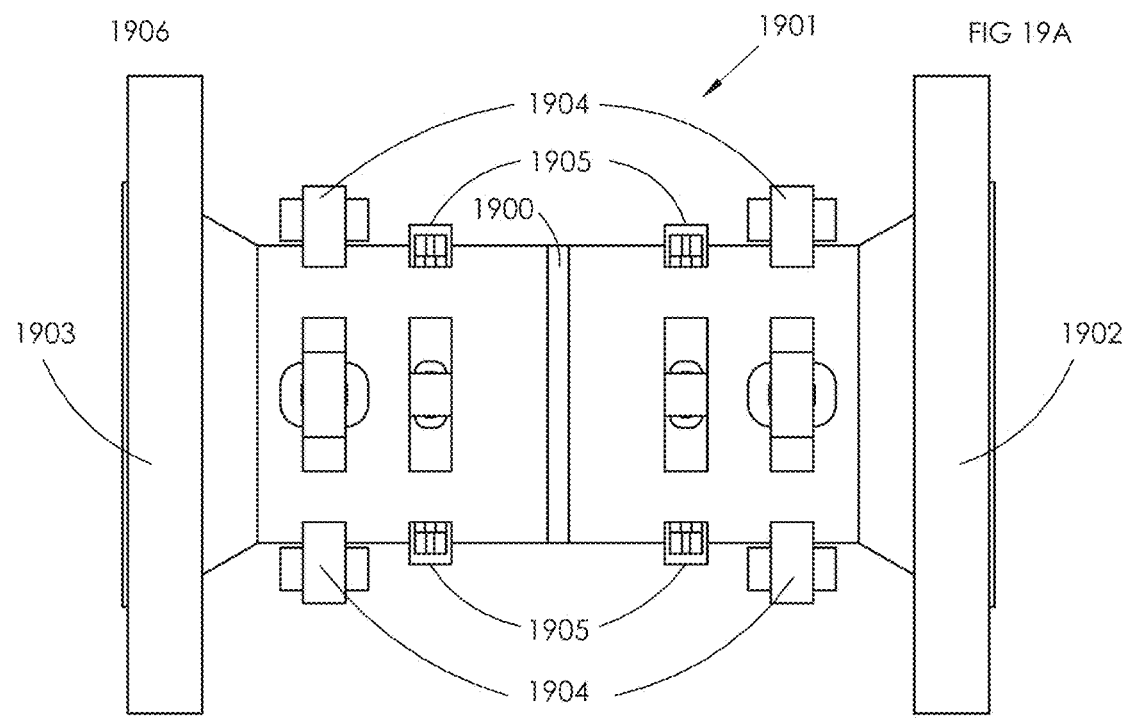
FIG. 19A is a side view of an example fluid parameter meter.
Figure 19B:
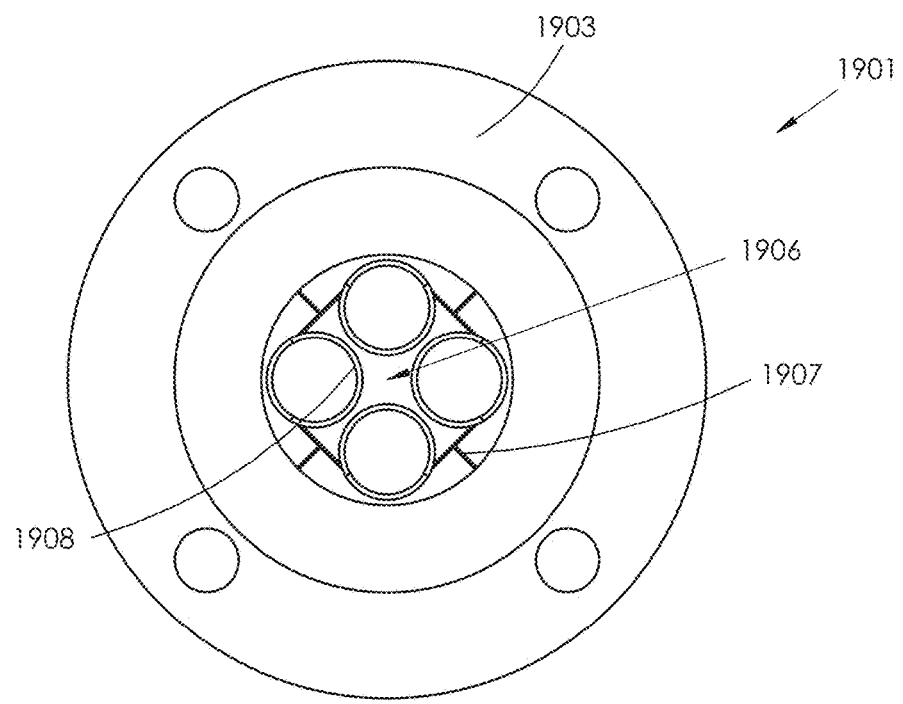
FIG. 19B is view down the fluid flow axis of an example fluid parameter meter as shown in FIG. 19A.

FIG. 19A is a side view of an example fluid parameter meter 1901. FIG. 19B is view down the fluid flow axis of an example fluid parameter meter 1901 as shown in FIG. 19A. The example fluid parameter meter 1901 includes flanges 1902 and 1903 which are weld neck flanges and for this example are 3 inch 150 pound ANSI long weld neck pipe flanges. In this example, flanges 102 and 103 are bolted to each other at center ring 1900 thereby forming a continuous conduit. Mounted in association with flanges 1902 and 1903 are electromagnetic driving assemblies 1904, and electromagnetic sensing assemblies 1905. Electromagnetic driving assemblies 1904 are arranged to cause radial mode vibrations on sensor element assembly 1906. Electromagnetic sensing assemblies 1905 are arranged to sense the radial mode vibrations on sensor element assembly 1906.

Figure 20:
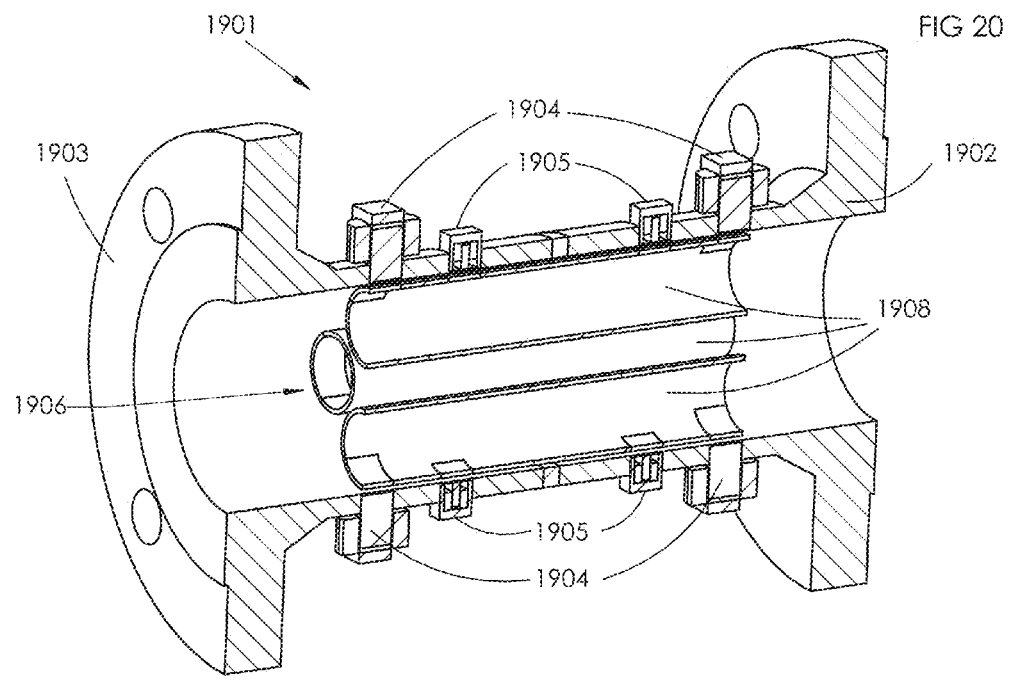
FIG. 20 is an oblique cross section view of an example fluid parameter meter as shown in FIG. 19A.
Figure 21:
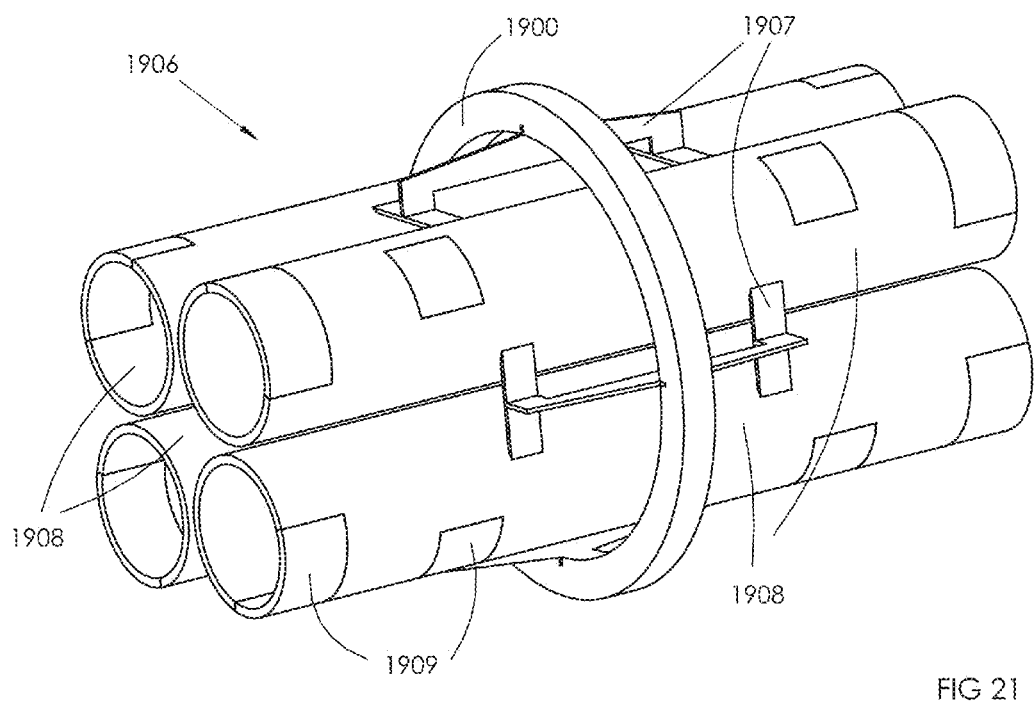
FIG. 21 is view of a sensor element assembly.

Sensor element assembly 1906 is more clearly shown in FIGS. 20 and 21. FIG. 20 is an oblique cross section view of an example fluid parameter meter as shown in FIG. 19A. FIG. 21 is view of a sensor element assembly 1906. The example sensor element assembly 1906 includes four sensor elements 1908 arranged in a pattern and held in place by four mounting flexures 1907. Some of mounting flexures 1907 are not visible in all views.

The example sensor element assembly 1906 is shown having four sensor elements 1908, however any numbers of sensor elements can be used, such as but not limited to, two or three or five or other numbers.

FIG. 20 is a cross section view of fluid parameter meter 1901 showing the sensor element assembly 1906 inside. Sensor elements 1908 are made of strong flexible material such as stainless steel but could also be made of other materials such as glass, plastic, ceramic, brass, and others. To enhance electromagnetic coupling between sensor elements 1908 and electromagnetic driving assemblies 1904, and electromagnetic sensing assemblies 1905, magnetic material can be incorporated into sensor elements 1908 such as magnetic inserts 1909 shown in FIG. 21. Magnetic inserts 1909 can be magnetic material such as iron, carbon steel, ferritic steel, duplex steel, 430-stainless steel, samarium cobalt, neodymium iron boron, alnico, and the like. In another example, sensor elements 1908 can be made of magnetic material such as carbon steel or iron or 430 stainless steel, or duplex steel, or other magnetic material without including magnetic inserts 1909. Magnetic inserts 1909 can be attached to sensor elements 1908 by welding, brazing, adhesion, clamping, or other attachment methods.

In an example method of operation, electromagnetic driving assemblies 1904 are activated by electronics (not shown) to cause the requisite forces on sensor element assembly 1906 thereby causing a radial motion as shown in FIGS. 22A and 22B.

FIGS. 22A and 22B are two views of an example sensor element assembly shown as finite element analysis deflected shapes due to radial mode vibration. FIG. 22A shows the proximal end of the top and bottom sensor elements 1908 are moving apart from each other while the proximal ends of the left and right sensor element ends are moving toward each other as shown by the motion arrows 1910. At the distal end the opposite motion is shown where the top and bottom sensor element ends 1908 are moving toward each other while the left and right sensor elements ends are moving away from each other as shown by the motion arrows 1910.

FIG. 22B shows the motion of FIG. 22A but delayed by 180 degrees of one vibration period and so all the just described motions are reversed.

In another example method of operation, electromagnetic driving assemblies 1904 are activated by electronics (not shown) to cause the requisite forces on sensor element assembly 1906 thereby causing a radial motion as shown in FIGS. 23A and 23B.

FIGS. 23A and 23B are two views of an example sensor element assembly shown as finite element analysis deflected shapes due to radial mode vibration. FIG. 23A shows the proximal end of the top and bottom sensor elements 1908 are moving toward each other while the proximal ends of the left and right sensor element ends are moving away from each other as shown by the motion arrows 1910. At the distal end the same motion is shown where the top and bottom sensor element ends 1908 are moving toward each other while the left and right sensor elements ends are moving away from each other as shown by the motion arrows 1910. FIG. 23B shows the motion of FIG. 23A but delayed by 180 degrees of one period.

Sensor assembly 1906 is similar to sensor assembly 600 previously described. On sensor assembly 1906, the radial motion of sensor elements 1908 is facilitated by flexing of mounting flexures 1907. Whereas On sensor assembly 600, the radial motion of sensor elements 601 and 603 is facilitated by flexing of flexures 602 in combination with sensor element 601. The resulting radial vibratory motion is the same in both cases in that sensor elements 1908 of sensor element assembly 1906 move in a radial motion as previously described and are thereby functional to measure fluid parameters including density, viscosity, flow rate, and others as was previously described for other embodiments.

Mounting flexures 1907 are made of strong flexible material such as metal, stainless steel, glass, plastic, fiberglass, composite or other material. Mounting flexures 1907 are designed to allow sensor assembly 1906 to vibrate in a radial motion having a natural mode of vibration similar to the motion just described for FIGS. 22A and 22B.

Mounting flexures 1907 may also be designed to allow sensor assembly 1906 to vibrate in another radial motion having a natural mode of vibration similar to the motion just described for FIGS. 23A and 23B.

In an example method of operation, sensor assembly 1906 is caused to vibrate by electromagnetic driving assemblies 1904 in a natural mode of vibration shape similar to that shown in FIGS. 22A and 22B where the motion of the proximal ends of sensor elements 1908 is reversed from the motion of the distal ends of the same sensor elements 1908. This reversal of motion from the proximal ends to the distal ends of sensor elements 1908 causes a rotational motion of any fluid that may be flowing through sensor elements 1908. This rotational motion combined with any flowing fluid motion causes Coriolis forces along the length of sensor elements 1908 which then deflect according to the magnitude of those Coriolis forces by a measurable amount "Coriolis motion", Electromagnetic sensing assemblies 1905 sense the driven motion of sensor elements 1908 in combination with any induced Coriolis motion. Signals from electromagnetic sensor elements 1908 can then be processed by electronics (not shown) to determine the flow rate of flowing fluid passing through fluid parameter meter 1901. In normal operation, to measure the flow rate of fluid passing through the fluid parameter meter 1901, signals from the electromagnetic sensor assemblies 1905 at the inlet end of the meter 1901 are compared to signals from the electromagnetic sensor assemblies 1905 at the outlet end of the meter 1901 for any time or phase difference there between. A time or phase difference between these signals is indicative of fluid flowrate passing through fluid parameter meter 1901.

In another example method of operation, signals from electromagnetic sensor assemblies 1905 can be converted to digital values by an analog to digital converter (not shown) and the resulting values can be mathematically manipulated to produce resulting values that are indicative of fluid parameters such as the flow rate, density, viscosity, Reynolds number, mass fraction, volume fraction, and others.

It is noted that the examples shown and described are provided for purposes of illustration and are not intended to be limiting. Still other examples are also contemplated.

The invention claimed is:

1. A fluid parameter meter to measure at least one parameter of a fluid, comprising:
   an outer conduit;
   a sensor element assembly disposed in said outer conduit and having a plurality of sensor elements to convey a portion of said fluid through said sensor element assembly;
   at least one mounting flexure fixedly attached to said sensor element assembly and to said outer conduit, said at least one mounting flexure configured to enable said sensor element assembly to vibrate in radial motion;
   at least one vibration driver arranged to cause said sensor element assembly to vibrate in said radial motion;
   at least one vibration sensor to sense said radial motion of said sensor element assembly; and
   controlling electronics operating in cooperation with said vibration driver, and operating in cooperation with said vibration sensor, and operating to said measure at least one parameter of a fluid based on said radial motion.

2. The fluid parameter meter of claim 1 where said radial motion of said inlet end of said sensor element assembly is reversed from said radial motion of said outlet end of said sensor element assembly.

3. The fluid parameter meter of claim 1 where said radial motion of said inlet end of said sensor element assembly is not reversed from said radial motion of said outlet end of said sensor element assembly.

4. The fluid parameter meter of claim 1 where said parameter of a fluid is a flow rate of said fluid.

5. The fluid parameter meter of claim 1 where said parameter of a fluid is a viscosity of said fluid.

6. The fluid parameter meter of claim 1 where said parameter of a fluid is a density of said fluid.

7. The fluid parameter meter of claim 1 where said parameter of a fluid is a Reynolds number of said fluid.

8. The fluid parameter meter of claim 1 where said parameter of a fluid is a volume fraction of said fluid.

9. The fluid parameter meter of claim 1 where said parameter of a fluid is a mass fraction of said fluid.

10. A fluid parameter meter to measure at least one parameter of a fluid, comprising:
    a sensor element assembly disposed in an outer conduit and having a plurality of sensor elements to convey a portion of said fluid through said sensor element assembly;
    at least one mounting flexure fixedly attached to said sensor element assembly and to said outer conduit, said at least one mounting flexure configured to enable said sensor element assembly to vibrate in radial motion;
    at least one vibration driver arranged to cause said sensor element assembly to vibrate in said radial motion; and
    at least one vibration sensor to sense said radial motion of said sensor element assembly.

11. The fluid parameter meter of claim 10 where said radial motion of said inlet end of said sensor element assembly is reversed from said radial motion of said outlet end of said sensor element assembly.

12. The fluid parameter meter of claim 10 where said radial motion of said inlet end of said sensor element assembly is not reversed from said radial motion of said outlet end of said sensor element assembly.

13. The fluid parameter meter of claim 10 where said parameter of a fluid is a flow rate of said fluid.

14. The fluid parameter meter of claim 10 where said parameter of a fluid is a viscosity of said fluid.

15. The fluid parameter meter of claim 10 where said parameter of a fluid is a density of said fluid.

16. The fluid parameter meter of claim 10 where said parameter of a fluid is a Reynolds number of said fluid.

17. The fluid parameter meter of claim 10 where said parameter of a fluid is a volume fraction of said fluid.

18. The fluid parameter meter of claim 10 where said parameter of a fluid is a mass fraction of said fluid.

* * * * *